(12) United States Patent
Shatkin et al.

(10) Patent No.: US 6,312,926 B1
(45) Date of Patent: Nov. 6, 2001

(54) MRNA CAPPING ENZYMES AND USES THEREOF

(75) Inventors: Aaron J. Shatkin, Scotch Plains; Renuka Pillutla, Edison; Danny Reinberg, Martinsville, all of NJ (US); Edio Maldonado, Santiago (CL); Zhenyu Yue, New York, NY (US)

(73) Assignee: University of Medicine & Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 09/134,218

(22) Filed: Aug. 14, 1998

(51) Int. Cl.⁷ .............................. C12P 19/34; C07H 21/04
(52) U.S. Cl. ................ 435/91.1; 435/193; 435/252.3; 435/254.11; 435/325; 435/320.1; 435/348; 435/349; 435/350; 435/351; 435/352; 435/353; 435/354; 435/358; 435/363; 435/366; 435/6; 536/23.1; 536/23.2; 536/23.5
(58) Field of Search .......................... 435/6, 91.1, 193, 435/252.3, 254.11, 325, 320.1, 348, 349, 350, 351, 352, 353, 354, 358, 363, 366; 536/23.1, 23.2, 23.5

(56) References Cited

PUBLICATIONS

Sigma Catalog (Jan. 1993) Catalog No. A2383, p. 48.*
Yue et al., (Nov. 1997) Mammalian capping enzyme complements mutant . . . . Proc. Natl. Acad. Sci. USA 94: 12898–12903.*
Yamada–Okaba et al. (Apr. 1998) Isolation and characterization of a human cDNA for . . . . Nucleic Acids Research 26 (7): 1700–1706.*
Tsukamoto et al. (Feb. 1998) Cloning and characterization of two human cDNAs encoding the mRNA capping enzyme. Biochemical Biophysical Research Communications 243 (1): 101–108.*
Ho et al. (Apr. 1998) The guanyltransferase domain of mammalian mRNA capping enzyme binds to the phosphorylated carboxyl–terminal domain of RNA polymerase II. J. Biol. Chem. 273 (16): 9577–9585.*

* cited by examiner

Primary Examiner—Rebecca E. Prouty
Assistant Examiner—Richard Hutson
(74) Attorney, Agent, or Firm—Klauber & Jackson

(57) ABSTRACT

The present invention provides an isolated nucleic acid encoding a mammalian capping enzyme. The present invention further provides an isolated nucleic acid encoding a mammalian (Guanine-7-) methyltransferase enzyme. The present invention also provides an isolated mammalian capping enzyme protein or subunit thereof. In addition the present invention provides an isolated mammalian (Guanine-7-) methyltransferase enzyme protein or portion thereof. The present invention further provides methods for catalyzing formation of RNA 5'-terminal GpppN cap complex and for coupled transcription, translation and formation of RNA 5'-terminal GpppN cap complex and methylated RNA 5'-terminal GpppN cap complex. Kits thereto are also provided.

26 Claims, 19 Drawing Sheets

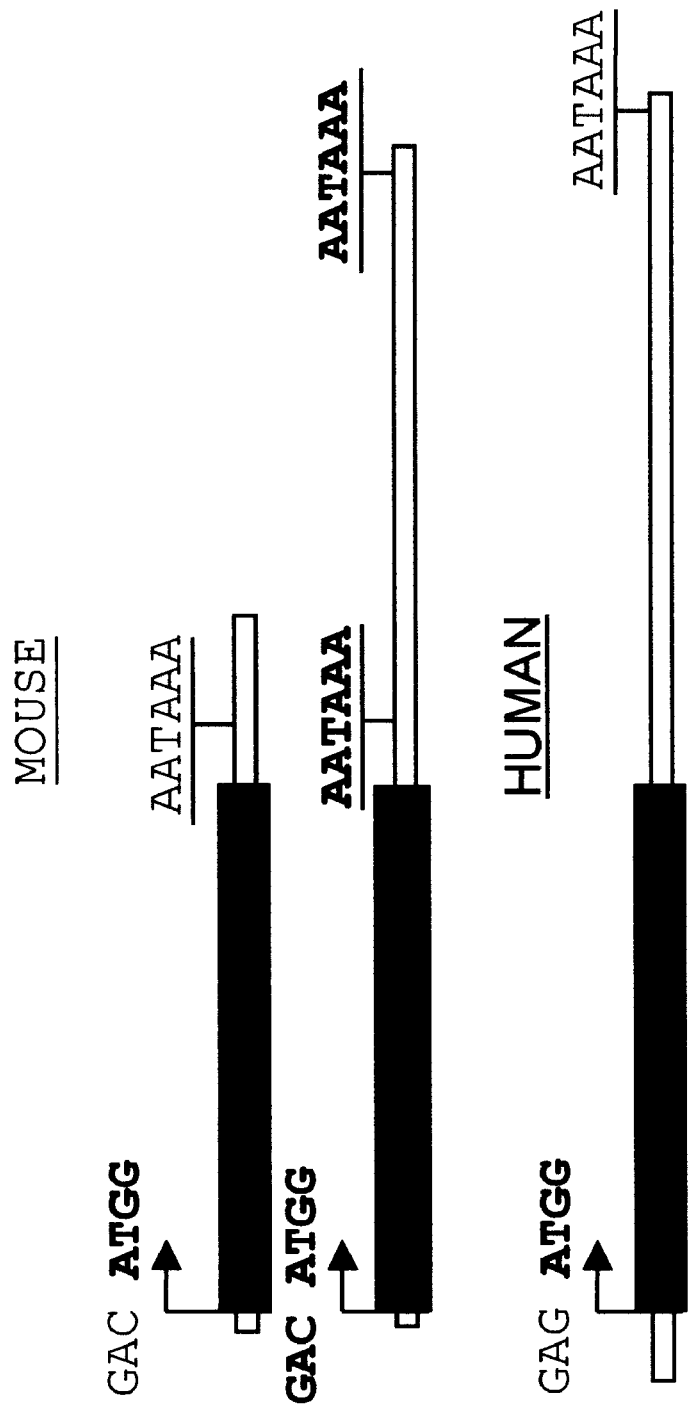

FIG. 1B-1

```
1    MAYNKIPPRWLNCPRRGQPVAGRFLPLKTMLGPRYDSQVAEENRFHPSMLSNYLKSLKVK    mouse
1    ...H..................................I...................    human 61   MSLLVDLTNTSRFYDRNDIEKEGIKYIKLQCKGHGECPTTENTETFIRLCERFNERSPPE    mouse
61   .G..........................................N.............    human 121  LIGVHCTHGFNRTGFLICAFLVEKMDWSIEAAVATFAQARPPGIYKGDYLKELFRRYGDI    mouse
121  ...........................................................    human 181  EEAPPPPVLPDWCFEDEDEEDEDGKKDSEPGSSASFSKRRKERLKLGAIFLEGITVKG    mouse
181  .L...........DED.........E...........G...................V...    human 241  VTQVTTQPKLGEVQQKCHQFCGWEGSGFPGAQPVSMDKQNIRLLEQKPYKVSWKADGTRY    mouse
241  ..................................K..DL...................    human 301  MMLIDGTNEVFMIDRDNSVFHVSNLEFPFRKDLRMHLSNTLLDGEMIIDKVNGQAVPRYL    mouse
301  ..........................................R................    human 361  IYDIIKFNAQPVGDCDFNIRLQCIEREIISPRHEKMKTGLIDKTQEPFSVRPKQFFDINI    mouse
361  .......S.............V.....................N.P...CT         human
```

FIG. 1B-2

```
421  SRKLLEGNFAKEVSHEMDGLIFQPIGKYKPGRCDDILKWKPPSLNSVDFRLKITRMGGEG    mouse
421  ...........................T................................    human 481  LLPQNVGLLYVGGYERPFAQIKVTKELKQYDNKIIECKFENNSWVFMRQRIDKSFPNAYN    mouse
481  ...P............................................T...........    human 541  TAMAVCNSISNPVTKEMLFEFIDRCAAAAQGQKRKYPLDPDTELMPPPPPKRLHRPT       mouse
541  .......T..S.........HH..................................PRPL.  human
```

FIG. 2A

```
232 FLEGVTVKGVTQVTTQPKLGEVQQKCHQF--CGWEGSSGFPGAQPVSMDKQ      human
232 FLEGITVKGVTQVTTQPKLGEVQQKCHQF--CGWEGSSGFPGAQPVSMDKQ      mouse
238 FMDGL-IRGVKVCEDEGKKKSMLQAKIKNL-QKYNKQGFPGLQPVSLSRG       C. elegans
  7 SRVAPEIPGLIQPGNVTQ---DLKMMVCKLLNSPKPTKTFPGSQPVSFQHS      S. cerevisiae
  7 DIEEVSVPGVLAPRDDVR---VLKTRIAKLLGTS--PDTFPGSQPVSFSKK      S. pombe 280 NIKL--LDLKPYKVSWKADGTRYMLI---------DGTNEVFMIDRDNSVFHV    human
280 NIRL--LEQKPYKVSWKADGTRYMLI---------DGTNEVFMIDRDNSVFHV    mouse
285 NINL--LEQESYMVSWKADGMRYIIYI--------NDG-DVYAFDRDNEVFEI    C. elegans
 55 DVEEKLLAHDYYVCEKTDGLRVLMF-LVINPVTGEQGC-FMIDRENNYYLV     S. cerevisiae
 53 HLQA--LKEKNYFVCEKSDGIRCLLYMTEHPRYENRPSVLFDRKMNFYHV      S. pombe 323 SNLEFPFRKD-----LRMHLSNTLLDGEMIIDRVNGQAV-------PRYLIY    human
323 SNLEFPFRKD-----LRMHLSNTLLDGEMIIDKVNGQAV-------PRYLIY    mouse
327 ENLDFVTKNG-----APHMETLVDTEVIIDKVEINGAMCDQPRMLIY         C. elegans
104 NGFREPRLPQKKEELLETLQDGTLLDGELVLQTNPMTKL--QELRYLMF       S. cerevisiae
102 EKIFYPVENDKSGKKY-----HVDTLLDGELVLDIYPGGK--KQLRYLVF      S. pombe 363 DIIKFNSQPVGDCDFNVRLQCIEREIISPRHEKMKTGLIDKTQEPFSVRN      human
363 DIIKFNAQPVGDCDFNIRLQCIEREIISPRHEKMKTGLIDKTQEPFSVRP      mouse
369 DIMRFNSVNMKEPEYKREFIIKTEIIDMRTAAFKTGRLKHENQIMSVRR       C. elegans
152 DCLAINGRCLTQSPTSSRIAHLGKEFFKPYFDLRAAYPNRCTFPFKISM       S. cerevisiae
145 DCLACDGIVYMSRLLDKRLGFAKSIQKPLDEYTKTHMRETAIFPELTSL       S. pombe
```

FIG. 2B

```
413 KPFFDICTSRKLLEGNFAKEVSHEMDGLIFQPT-GKYKPGRCDDIL-KWK    human
413 KQFFDINISRKLLEGNFAKEVSHEMDGLIFQPI-GKYKPGRCDDIL-KWK    mouse
419 KDEYDLEATAKLFGPKEVQHVGHEIDGLIFQPKKTKYETGRCDKVL-KWK    C.elegans
202 KHMDFSYQLVKV-AKSLDK-LPHLSDGLIFTPVKAPYTAGGKDSLLIKWK    S.cerevisiae
195 KKMELGHGILKLFNEVIPR-LRHGNDGLIFTCIETPYVSGTDQSLL-KWK    S.pombe 461 PPSLNSVDFRLKIT-RMGGEGLLPP--------------NVGLLY------   human
461 PPSLNSVDFRLKIT-RMGGEGLLPQ--------------NVGLLY------   mouse
468 PPSHNSVDFLLKVE-KKCKEGMLPE--------------WIGYLF------   C.elegans
250 PEQENTVDFKLLIDIPMVEDPSLPKDDRNRWYYNYDVKPVFSLYVWQGGA-   S.cerevisiae
243 PKEMNTIDEMLKLEFAQPEEGDI---------DYSAMPEQLGVWEG-----   S.pombe 491 --------VGGYERPFAQIKVT-------------------KELKQYD-N    human
491 --------VGGYERPFAQIKVT-------------------KELKQYD-N    mouse
498 --------VQNLSDPFGTMKAT-------------------ATLKKYH-N    C.elegans
300 DVNSRLKHFDQPFDRKEFEILERTYRKFAELSVSDEEWQNLKNLEQPLNG    S.cerevisiae
281 ----------RNMYSF-------FAFMYVDEKEWEKLKSFNVPLSE----    S.pombe 513 KIIECKF-----------ENNSWVFMRQRTDKSFPNAYNTAMAVCNSISNPVTKE    human
513 KIIECKF-----------ENNSWVFMRQRTDKSFPNAYNTAMAVCNSISNPVTKE    mouse
520 KIIECTLLVDNQGRPKEWKEMRERTDKSLPNGLRTAENVVETMVNPVTET    C.elegans
350 RIVECAK-------NQETGAWEMLRFRDDKLNGNHTSVVQKVLESINDSVSLF    S.cerevisiae
310 RIVECYL-------DDEN-RWRELRFRDDKRDANHISTVKSVLQSIEDGVSKE    S.pombe
```

FIG. 2C

```
557  ML FE------------F I DRC T AA S Q GKR KH H L D P D TELMPPPKR PR P L T    human
557  ML FE------------F I DRCAAAA Q GKR KY P L D P D TELMPPPKR L HR P T    mouse
570       YL IE                                                            C.elegans
396  DL EE I VGD I KRCWDE RR AN MA GG S GR P L PSQ QNATLSTSK P VHSQ PP SN   S.cerevisiae
355  DL L KEMP I I REAYYNR K--KPSVT KR KL D ET S ND-------DA PA I           S.pombe 597  DKEPKYVDEDDWSD        human
597                        mouse
573                        C.elegans
446  KKVAK---ESEKEI        S.cerevisiae
392                        S.pombe
```

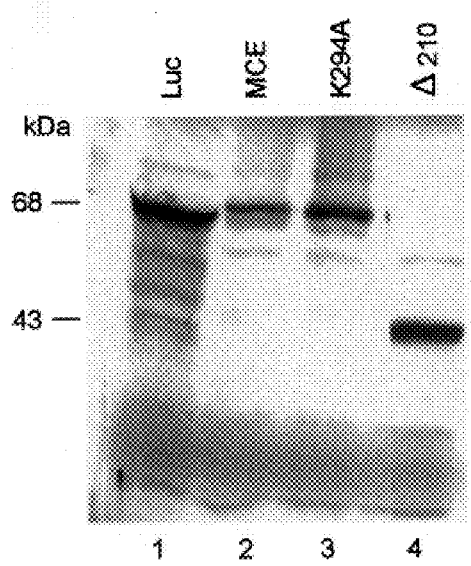 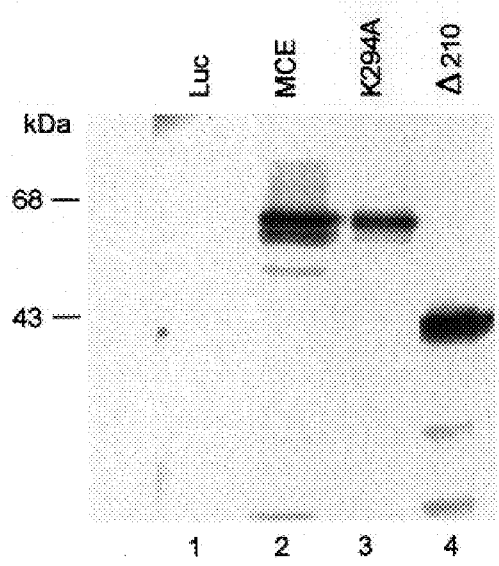

FIG. 9A

```
1     MA-NSAKAEEYEKMSLEQAKASVNSETESSFNINENTTASGTGLSEKTSVC    hmet.pep
1     MS------LNYEQNAADE-------------------------------    cel_met.pep
1     MM-K---------------------------------------------    dros_met.pep
1     MSTKPEKPIWMSQEDYDRQYGSITGDESSTVSKKDSKVTANAPGDGNGSL-    ABD1.pep 1     RQVDIARKRKFEDDLVKESSSCGKDTPSKKRKLDPEIVPEEKDCGDAEGN    hmet.pep
13    ---QFARAHKAV---SLSDDEESEGQAETTSAPNQEPHV-----------    cel_met.pep
4     ---------------------------EVLDAFRKSGEAEGF-------    dros_met.pep
51    PVLQSSILTSKVSDLPIEAESGFKIQKRRHERYDCE--------------    ABD1.pep 102   SKKRKRETEDVPKDKSSTGDGTQNKRKIALEDVPEKQKNLEEGHSSTVAAH    hmet.pep
46    -SKSPREYYDEPGGKGN-GSGADD--------QDEPETEAASGAANTHVAHH    cel_met.pep
19    GHNKMS-------------------------------SSEVASH    dros_met.pep
88    --------ERLRKQRAQKLREEQLKR-------HEIEMTANRSINVDQIVREH    ABD1.pep 153   YNELQEVG-LEKRSQSRIFYLRNFNNWMKSVLIGEFLEKVRQKKKRD--IT    hmet.pep
89    YNELKEAG-RKDROQKSKIFFMRNFENNWIKSQLINEYMSQIKQNKRMGDALR    cel_met.pep
32    YNKVLQVG-IEGRKESRIFFMRNMNNWVKSQLINDAKQRVNDG--VNNPR    dros_met.pep
126   YNERTIIANRAKRNLSPIIKLRNFNNAIKYMLIDKYTKPGD---------V    ABD1.pep
```

FIG. 9B

```
                                                                                                        I
201  VLDLGCGKGGDLLKWKKGRINKLVCTDIADVSVKQQQQRYEDMKNRD-SE       hmet.pep
139  VLDMCCGKGGDLLKWEKAAISHLICTDIAEVSVEQCQRRYQDILQRSEKSK      cel_met.pep
 80  VLDIACGKGGDLKKWDIAGAKDVVMADVSIQQAEERYKQMFGYKKN--         dros_met.pep
168  VLELGCGKGGDLRKYGAAGISQFIGIDISNASIQEAHKRYRSMRN-D----      ABD1.pep 251  YI--FSAEFITADSSKELL---IDKFRDPQMCFEDICSCQFVCHYSFESYEQ     hmet.pep
190  FANKFTAEFFACDSTLVRL---RERYKDPSLQLNLVSCQFAEHYCFESMAQ      cel_met.pep
129  --NIFTVQFIVADCTKENL---EDRIENKD-PFDLVSCQFALHYSFVDEAS      dros_met.pep
215  ----YQVVLITGDCFGESLGVAVEPFPDCRFPCDIVSTQFCLHYAFETEEK      ABD1.pep
                                   III
297  ADMMLRNACERLSPGGYFIGTTPNSFELIRRLE--ASETES--FGNELYTV      hmet.pep
238  ADCMRNAAECLKPGGFFIATMPDAYEIIRRLR--AAGPDARRFGNDVYSI       cel_met.pep
174  ARIFLKNAVGMLKPGGVFIGTLPDADRIVWSMR---NGENG--CFANEVCKL     dros_met.pep
262  ARRALINVAKSLKIGGHFFGTIPDSEFIRYKLNKEPKFEVKPSWGNSIYKV      ABD1.pep 344  KFQ-----KKGDYPL----FGCKYDFNLEGVVD-VPEFLVYFPLLNEMAKKY     hmet.pep
287  EFDC-----ETDPLPL----FGAKYQFHLEGVVD-CPEFLVHFPTLVKLGRKY    cel_met.pep
221  TYEN-VEELAEGKVPL----FGAKFHESLDEQVN-CPEFLAYFPLVKHLLEEL    dros_met.pep
313  TFEN-NSYQKNDYFTSPYGQMYTWLEDAIDNVPEYVVPFETLRSLADEY        ABD1.pep
```

FIG. 9C

```
386 NMKLVYKKTFLEFYEEKIKNNENKMLLKRMQALEPYPANESSKLVSEKVDD    hmet.pep
330 GLQLLKRSTFADYYKENL----HHGRHLLQRMSGLESVQPQRC----ENDEE   cel_met.pep
268 DMELLFVHNFAEAINKWL---EPGRRLLESMTGLETYPNE----KLSGKSDDE  dros_met.pep
363 GLELVSQMPENKFVQEIPKW ERFSPKMREGLQ----------RSDGR       ABD1.pep x
437 Y-----EHAAKYMKNSQVRLPLGTLSKSEWEATSIY----LVFAFEKQQ      hmet.pep
374 F----AHVSNFQGAQRSR-SVGTLSKSEWEAASEETQHRLLNSITK         cel_met.pep
314 YLEAKAKLDAFPEDERIK-TMGTLSKSEWEATCMY----LVFGFRKKKSEA    dros_met.pep
402 Y-----GVEGDEKEAASYFYT---MFAFRK                         ABD1.pep 476 EKTEEEPATTKPVAESESEQKEVTESEEKEDQEDCEHQEAQTN            hmet.pep
414 VKQYIEPESVKP-------------------------------N           cel_met.pep
360 --------------------------------------------           dros_met.pep
424 --------------------------------------------           ABD1.pep
```

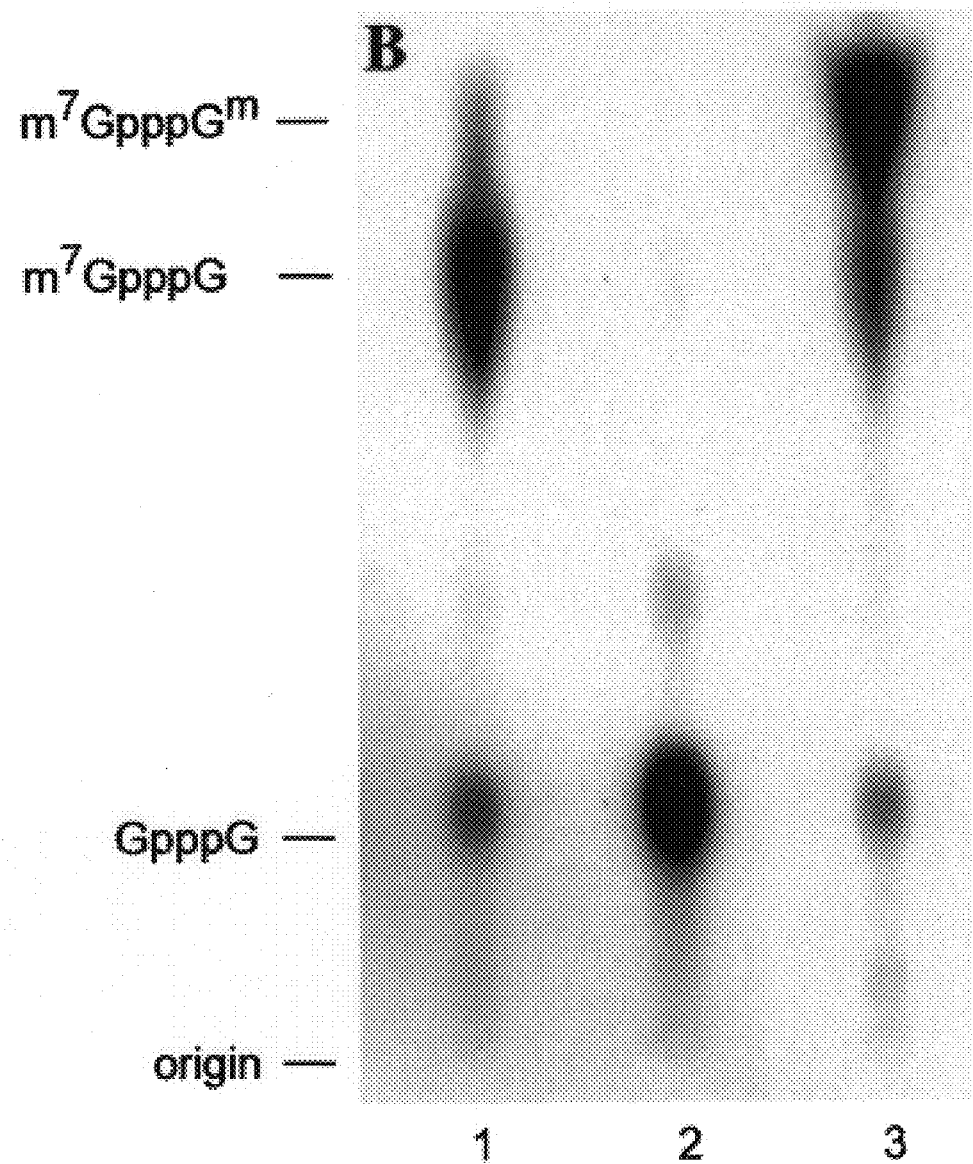

SEQUENCE LISTING

```
<160> NUMBER OF SEQ ID NOS: 19

<210> SEQ ID NO 1
<211> LENGTH: 4160
<212> TYPE: DNA
<213> ORGANISM: Mus musculus

<400> SEQUENCE: 1
gctgtggagc tatcggcgag gcggcacaga catggcttac aacaagatcc cgccgcggtg      60
gctgaactgt ccgcggcgcg gtcagccggt ggcaggaaga ttcttacctc tgaagacgat     120
gctggggcca agatatgata gtcaagttgc tgaagaaaac cggttccatc ccagtatgct     180
ctcaaattat ctaaagagcc tgaaggttaa aatgagcttg ttggtggatc tgacaaatac     240
ttcaaggttc tatgacagaa atgacataga aaagaaggaa atcaagtata tcaaacttca     300
gtgtaaagga catggcgaat gccccaccac tgagaatact gagacattca ttcgcctgtg     360
tgagaggttt aatgaaagaa gcccacctga acttataggt gttcactgca cccatggctt     420
caaccgtact ggtttcctta tatgtgcctt tttggtggaa aaaatggatt ggagtattga     480
agcagcagtt gctacatttg cccaagccag accaccagga atctacaagg gtgattattt     540
gaaggaactt tttcgtcgct atggagatat agaagaagca ccaccaccac ctgtattgcc     600
agattggtgt tttgaagatg aggatgaaga agatgaggat gaagatggaa aaaaggactc     660
agaaccaggg tcaagtgcat cctttagtaa aaggagaaaa gagcggttaa aactgggagc     720
tattttcttg gaaggcataa ctgttaaagg tgtaactcaa gtaacaactc aacccaagtt     780
aggagaggtg cagcagaaat gtcatcagtt ctgtggctgg gaagggtctg ggttccctgg     840
agcacagcct gtctccatgg acaagcaaaa tattagactt ttagagcaga agccttataa     900
agtaagctgg aaagcagacg gcactcgtta catgatgttg attgatggca caatgaagt      960 ttttatgatt gacagagata attccgtttt tcatgtttca aatctggaat ttccatttcg    1020
taaagatctt cgcatgcatt tatcaaatac tctttttggat ggggaaatga tcattgacaa    1080
agtaaatgga caggccgtcc caagatattt gatctatgac ataattaagt tcaatgcaca    1140
accagttgga gactgtgatt ttaatattcg tctacagtgt attgaacgtg aaattataag    1200
tccacgacat gaaaaaatga agactggact cattgacaaa acacaggaac catttagtgt    1260
cagacctaaa caatttttg acatcaatat ttcaagaaag cttctggaag gaattttgc     1320 caaagaagtc agccatgaaa tggatggact tattttcag cctattggaa aatacaagcc    1380
tggtcgatgt gatgacattt tgaaatggaa acctcccagt ctaaactctg tggattttcg    1440
acttaagata acaagaatgg gaggagaagg gttgcttcca cagaatgttg gccttctcta    1500
tgttggaggt tatgaaagac cctttgcaca aatcaaggtg acaaaagaac taaaacagta    1560
tgacaacaaa attatagaat gcaaatttga gaacaatagc tgggtcttca tgagacagag    1620
gatagacaaa agtttcccaa atgcctacaa cacagccatg gctgtgtgca atagcatctc    1680
```

```
gaaccctgtc accaaggaga tgctgtttga attcattgac agatgtgcag cagccgccca      1740
gggacagaag cggaagtatc ccctggaccc tgacacggag ctcatgccgc ccccaccgcc      1800
caaaagactg catcggccaa cctagtccgt gcctctgaga ggaagaaaaa tgctgttgtc      1860
tcattttctc aaccagagaa attaaagaga cgagcggctt cgtactggta cacgtgtttt      1920
aagggaagac atagtcagcc tgtatatatt tggtagtccg tgcctctgag aggaagaaaa      1980
atgctgttgt ctcatttttct caaccagaga attaaagag acgagcggct tcgtactggt      2040
acacgtgttt taagggaaga catagtcagc ctgtatatat ttggtacatt tggtttcctt      2100
ggaactacag tacatcatgg acctaaatat tttatttata cctgaataaa ttcagcctta      2160
ccctgtggag tctacagatt gaaataccca aaggttaaat cagattgaag ttaatgaaat      2220
agagcctgtt tgtatgtgaa tagatacctt tacatttgat tcataactag caatctgaag      2280
ctgtaagcat attgagtttt ttaaatgttg gattttaagt ttacctcttt aaaatgtggg      2340
tactggcatt agaaattttc tcactaactt atcatggatt tcttatattt ctcaattttt      2400
tatattctga gcaatgacaa ggtcaagtat tatgtacatt aaacagtttg gtctggctat      2460
accattttaa gaagttcttc tggttttgtt ttctgtgaga gtggggtgta aaaacagtaa      2520
tgaagctcca ttttcttgtg aattgtatcc tttctttaga aactattttg agcatttttac     2580 tatgtctcgt gtttgaacca tgacgtcaga tgtctggggt tcccatcctg gcagtggttt      2640
tgagttcctt tgtggcactt accttcatgt gctgctgtct gggagagttg ctgcctttca      2700
gacagcaggg ctcctcctgc tttacccact cactgtgatc cctgggaaca gcagcaagca      2760
caaccgcgtt gtgttaattt ccctcaaaca gtgcttcaga tgtcagctga acaaatgttg      2820
tctaggagat gctggcctcc catggacaga tgcagaggcg ttgctgagac tggtcatgga      2880
ggacgtgaag atgttgctcc cactgctcct gctgcacctg cgcttggagg tggtttccga      2940
tcctgagctg cacctcagcg ttgactctgg acagtaggtc cctgccgttg taaaacttgt      3000
tctgattggc ttgtgaagga attcagaata gcaactagca agcagcttac ttaatgtatt      3060
tattttagag acacaggttt taagtatatg tatttaaaac aaatgttcac gatctgtatt      3120
ttatatatgt attaagcata tctgaaagta tatgcaacag tgtatattcc tatattgata      3180
cagcccgaaa tgaaaatcca atgctttacc tagcagctaa gatctgatgg aattttatt      3240 tggccaagtt cagattaacc caaactgttt ttatattgaa cctgaatttt aatgttttta      3300
aacgaacttt acatctgccg tgcttttccg tttggaatac tagggctgtt cctagaaact      3360
tatgccgcca ttgttcccag ttaagttaaa agttagccag tttatcccaa atgccataat      3420
aattttgtct taggttgctt ttgtacattt gggcactgaa ggaatttaaa cacctgactg      3480
ttacaggatt gttgagggga gattgtcaag gttccttctg tcgtttacat ggtggatcca      3540
gaactgcctg tggactccag gcagcctagt gcctgctccc cagggtcact gatcttttct      3600
ccatagatgg tctgctccca agccggtgca aaagcggggt ccttttgaag atacagtaac      3660
gtgctttgtc agtgatctct gatagaatta aaatgttatg gtaacattaa cctttcaaat      3720
gaaatggaaa gagcattata taggacttac ttttttcagct tatcctttcc tttcaattgt      3780
ggtgacgtaa tcattggctt aaaagcagac cccatgtagt cccaaacgca tcacctctgg      3840
gggtatccta acaagccatt taggctgttg gacgaaaggt aggatttgga catcttgaag      3900
gaaaacttcc cttttcggct tatgttacaa cagctgtttt ctttagctga tatttttccag    3960 acaggactaa gaagactgtt tccctgagtt atcgcatggg aaggcttgct ttttgtttgg     4020
```

```
ggaaaaaaaa atatggatga ctactgccta gatggttcct ttgctttcca tgaaatgcca      4080
ggacattcct tctctgattg tgtcagtgtg tgttgtaata agctactga tgtaaaaaaa      4140 aaaaaaaaaa aaaaaaaaaa                                                  4160

<210> SEQ ID NO 2
<211> LENGTH: 4546
<212> TYPE: DNA
<213> ORGANISM: Homo sapiens

<400> SEQUENCE: 2
taccagtttg aatacatggc ccagcacctg gtgtttgcca actgcattcc tttgatccta       60
aagttcttca atcaaaacat catgtcctac atcactgcca agaacagcat ttctgtcctg      120
aatgaaagtg gcgcgccgcc cctgacgtta cccggatcgg agaggttgga attcagatta      180
cggctgcgat tcgggtgtct cggacccgg tgtgcaccgg accacgggga ggcggctcca       240
aaggcgcggt gaacgttggt gagggagggc agctctgcgc cccaagagat ggctcacaac      300
aagatcccgc cgcggtggct gaactgtccc cggcgcggcc agccgtggc aggaagattc       360 ttacctctga agacaatatt aggaccaaga tatgatagtc aagttgctga gaaaatcgg      420 ttccatccca gcatgctctc aaattaccta aagagcctaa aggttaaaat gggcttgttg      480
gtggacctga caaatacttc aaggttctat gaccgaaatg acatagaaaa agaaggaatc      540
aaatatataa aacttcagtg taaaggacat ggtgagtgcc ctaccactga gaatactgag      600
acctttattc gtctgtgtga gcggtttaat gaaagaaatc cgcctgaact tataggtgtt      660
cattgtactc atggcttcaa tcgcactggt ttcctcatat gtgccttttt ggtggagaaa      720
atggattgga gtatcgaagc agcagttgct acttttgccc aagccagacc accaggaatc      780
tacaagggtg attatttgaa ggaactttt cgtcggtatg gtgacataga ggaagcacca      840
cccccacctc tattgccaga ttggtgtttt gaggatgatg aagacgaaga tgaggatgag      900
gatggaaaga aggaatcaga acccgggtca agtgcttctt ttggcaaaag gagaaaagaa      960
cggttaaaac tggcgctat tttcttggaa ggtgttactg ttaaaggtgt aactcaagta     1020
acaacacaac caaagttagg agaggtacag cagaagtgtc atcaattctg tggctgggaa     1080
gggtctggat tccctggagc acagcctgtt tccatggaca gcaaaatat taaactttta     1140 gacctgaagc catacaaagt aagctggaaa gcagatggta ctcggtacat gatgttgatt     1200
gatggcacaa atgaagttt tatgattgat agagacaatt cagtatttca tgtttcaaat     1260 ctggaattc catttcgtaa agatcttcgt atgcatttat caaatactct cttggatggc     1320
gagatgatta ttgacagagt aaatggacag gctgttccta gatatttgat atatgacata     1380
attaaattca attcacagcc cgttggagat tgtgattta atgttcgtct gcagtgtata     1440
gaacgagaaa ttataagtcc tcgacacgaa aaatgaaga ctgggctcat tgacaaaaca     1500
caggaaccat ttagcgtcag aaataagccg tttttgaca tctgtacttc aagaaagcta     1560
cttgaaggaa atttttgcca agaagtgagc catgaaatgg atggacttat ttttcagcct     1620
actggaaaat acaaacctgg tcgatgtgat gatatttga atggaagcc tcccagtctg     1680 aattctgtgg attttcgtct aaaataacc agaatgggag gagaagggtt acttcctccg     1740
aatgttggcc tcctgtatgt tggaggttat gaaagaccct ttgcacaaat caaggtgaca     1800
aaagagctga acagtatga caacaaaatt atagaatgca aatttgagaa caacagctgg     1860
gtcttcatga gacagagaac agacaaaagt tttcctaatg cctacaacac tgccatggct     1920
gtgtgtaaca gcatctcaaa ccctgtcacc aaggagatgc tgtttgagtt catcgacaga     1980
```

-continued

```
tgtactgcag cttctcaagg acagaagcga aacatcatc tggaccctga cacggagctc    2040
atgccaccac cacctcccaa agaccacgc cctttaacct aagacctgcc tgtgacttga    2100
gggttaagaa gaaagaggaa tgaggaaaaa acgctgttgc ccattttgt cgccgagaaa    2160 ttgaaaaacg actgtggctt gatgttgata cacatttgaa attttttta aaaaaaaga    2220 attatcgtag ccagcctgta aatacttgat gcattcgttt cctcagtgct gcaatacatc    2280
atggacttaa acatcttatt tatctgataa actcagcctt accttgtgga atctgaagat    2340
tgaaatatcc aaggttttaa acaagatgga atcaatgaa aaagaggcct tgtttatata    2400
tgggtagctt cacatttaat ttataaagtt aacaatctgg aaactgtgag cccataaaac    2460
agtatttttt agaagttgtg ttacaactgt agcaaatttt cctttaaaa aatccaggca    2520 atggcattaa acattcttgc tatcatttac catggatttc ctacatttct gagatccctg    2580
tattcaaaaa caaatgacag ggttgttaag ttgtactata ttaaacaact tggtctggtt    2640
tatatcattt taacaagttt tttggaaatg taaagaaaa aagtaaagct ccattttgt    2700 gaattgcatt gtttctaaag gaagtatttt gagtatttc atctgtttgt attgtttcga    2760
ctatgatatc agatatccag tgtgtccatt ctggcagtgg ttttgagtta cttcatggaa    2820
cttggacata caccaccagg tcctttatgt gttgttctcc tgggagactt ctttttttaa    2880
atgccaggct acttctgctt tacctcagtg gtatcagcac attgttaatt acgttaaaac    2940
acacaactca ctgtgatcta tgggagtgat atcaaataca aacgatgttg tgttccttct    3000
ctcgaacaaa acagcaaagg gaatgccagc taacttcttt gattagaagg taatgtcatg    3060
gaatagaatg ctgtcaccag aaaatgctct cccactgcta gataaatgca gaggcaaagt    3120
gtagacatct gtaggaacta aatatcaagg aaatcaagac atttatttc aaagcgagaa    3180 ttctatctac attctattct gcggatgtta tttctgttat acatctgaat tttaaaatgt    3240
ttactgatag ataatggatt taagggcgg ctaattgatt gtctgccatt gttgataaac    3300
tgttctaatt ggtttgtgaa agaactctga gaattagcta aatggaggct agtgtattta    3360
tttttagagg tacatgtttt aagtaaatgt atttaaaaca aattttcatg gtctgaattg    3420
tatatgtaaa tgcatatctg tgtaagtata tgcaagtgta tattctttct actgatttca    3480
gtcagacacg aaatccaact gaattacccg gtagactgaa tatctgacgg gatttctata    3540
tggacatagc acagatgaac caaaaatgta tttatattca cctgagtttt aatgttttta    3600
aacaaagttt tctcctgcag tgcttttcta tatgaaatag ttgagtcaag cttgggcttt    3660
tttcttcgtt gttcccaagt catgtaatgt atagtgaatt tatccaaaac gccattgtaa    3720
cgttttttac tagagtgttt ttgcacattt gggcgctaaa gggattaaaa caactgatgc    3780
cacaatgact attgaaggag ggaaaattct caaggttcca tagtatcttt acaaaatgga    3840
ttaaaaaaaa atgcctatgc aacttcaaat agtctgatgc ctgcttcccc aggacgagtg    3900
actcttccac ggtgtgctgc tttccctccg agcctgtgga aaggcagagc ccttttgcag    3960
atacgaaagc aagcttttgc caatgatctt taatggagtt aaaatgttta tggtaattgt    4020
aacctttcaa atgagttacg tgaaagagc atctcacttt taatacaccc agatattttc    4080
ttcaagtctt tgcgcatttt tagcaggact taattttcct aaatttattc tttccttca    4140 attatagtga catagagtag ttggccttat aagtagatcc catttagccc ctgaacataa    4200
taccatctgc agtattataa aagtcattta gaaggtcagg gggataatct agaggcagga    4260
ttttggacat tgtgaaggaa atgtgctcct tctcagctca cttcaataac tattttctga    4320
```

-continued

| | |
|---|---|
| gactgaagtt ttttagacaa gaataagaaa actttgcttt cttcagttat cacatgtgaa | 4380 |
| agcttttgct ttttgttagg aaaaggtgtg gatgactcta ctgcgtggat ggttacattt | 4440 |
| gctttccgtg aaatgctcag aaaatgtcag gacattcctt ttccaattgt gtgtcagtgc | 4500 |
| gtattgtaat aaaactactg atggaattcc ggaaaaaaaa aaaaaa | 4546 |

<210> SEQ ID NO 3
<211> LENGTH: 6203
<212> TYPE: DNA
<213> ORGANISM: Homo sapiens

<400> SEQUENCE: 3

| | |
|---|---|
| aacagaatcg cgtttggctg tgctggatgt gtgaacctat tgggtactgt acaacttcaa | 60 |
| gcctcgaaat cagataggca ccaccaacct catttcctgt ttcaccttga ttttctgtga | 120 |
| taccaaaatc tcagcttcac aaagtcattg aaagtgttgg ttcatgaagt tttaccatca | 180 |
| attcaagtaa tcataaatgg caaattctgc aaaagcagaa gaatatgaaa agatgtctct | 240 |
| tgaacaggca aaagcgtcag tgaattctga acagagtct tcattcaata ttaatgaaaa | 300 |
| cacaacagct tctgggactg gctttctga aaagacttct gtctgtaggc aagtagacat | 360 |
| agcaagaaag agaaaagagt ttgaagatga tcttgtaaag gaaagttcta gttgtgggaa | 420 |
| agacactcca tccaagaaga gaaaacttga tcctgaaatt gtcccagagg aaaaagattg | 480 |
| tggtgatgct gaaggcaatt caaagaaaag aaaaagagaa actgaggatg ttccaaaaga | 540 |
| taaatcttct actggagatg gcactcaaaa taagagaaaa atagcacttg aggatgttcc | 600 |
| tgaaaagcag aaaaatctgg aagaaggaca cagctcaaca gtggctgccc attacaatga | 660 |
| acttcaggaa gttggtttgg agaagcgtag tcaaagtcgt atttttttacc taagaaactt | 720 |
| taataattgg atgaaaagtg ttctcattgg agaattttg gaaaaggtac gacagaagaa | 780 |
| aaaacgtgat atcactgttt tggacctggg atgtggtaaa ggtggagatt tgctgaaatg | 840 |
| gaaaaaagga agaattaaca agctagtttg tactgatatt gccgatgttt ctgtcaaaca | 900 |
| gtgtcagcag cggtatgagg acatgaaaaa tcgtcgtgat agtgaatata ttttcagtgc | 960 |
| agaatttata actgctgaca gctcaaagga acttctgatt gacaaatttc gtgacccaca | 1020 |
| aatgtgtttt gacatctgca gttgtcagtt tgtctgtcat tactcatttg agtcttatga | 1080 |
| gcaggctgac atgatgctga gaaatgcgtg tgagagactt agccctgggg gctatttat | 1140 |
| tggtactact cccaatagct ttgaattgat aagacgcctt gaagcttcag aaacagaatc | 1200 |
| atttggaaat gaaatatata ctgtgaaatt tcagaagaaa ggagattatc ctttatttgg | 1260 |
| ctgcaaatat gacttcaact tggaaggtgt tgtggatgtt cctgaattct tggtctattt | 1320 |
| tccattgcta aatgaaatgg caaagaagta caatatgaaa ctagtctaca aaaaaacatt | 1380 |
| tctggaattc tacgaagaaa agattaagaa caatgaaaat aaaatgctct aaaacgaat | 1440 |
| gcaggccttg gagccatatc ctgcaaatga gagttctaaa cttgtctctg agaaggtgga | 1500 |
| tgactatgaa catgcagcaa agtacatgaa gaacagtcaa gtaaggttac ctttgggaac | 1560 |
| cttaagtaaa tcagaatggg aagctacaag tatttacttg gtgtttgcct ttgagaaaca | 1620 |
| gcagtgagca cataggcagt agtcccgag gggccgtgtt ctgtcctgca caaatttgaa | 1680 |
| caactcatct cgatatattt gatatttctc tgtctgttga ttttaattct aaatgtgcag | 1740 |
| gatgctgcca gaaactccaa tgtagaaatt caacatttgc tgtctgtgac agatgaactt | 1800 |
| ttgcatgtgt atataagaat gagttgggac ctctgtcttt aaaaatctat ttttaggtaa | 1860 |
| tgttctaaga attccatttg cctctatgat cttagctcat aaaaatataa tatgacttga | 1920 |

```
taaagcaact aaactcttcc cacagtgttc agatttgtcc tgtgtgtgtt tacagtattc  1980
aatttattgc agttatagaa ttggtcagag agcattttca tagtgtgctc atttctatgg  2040
ttttgttata tagcattttt caacatttaa tggtctgtac agttgaatgt aagtgttcaa  2100
tatgtattgc tgaagttata agtttaaaac tcaatttcag atgctcataa aagttactta  2160
gctaaaattt tagcaattta ttgcattttg aaataatcat taacatgctg caattcagga  2220
gctggttaga acattttaag tggcagcata gaattttgga attttggggc tttcttttca  2280
gaaattgcta ccatagtaat taatgtttcc agttatcaag attgtgatta gacacattta  2340
cctttcttca ttgaacaaat ggtgccatag ttatttttct caaaatttag tgaaaatccc  2400
tcccatgtag acatgttgca cattttttcc aaatttatac atggaactgc agtaggaata  2460
ttctcaccat ctgatgccat gtacccactt cagaaataag caatacttgt tcctctgtta  2520
caacctcagc actttgcacc gtaggagcca ttgttaaagt tgtcacttgt gtaactgact  2580
gcttttccaa aactggtact tacgtgaact gttgtccttg ctttacacca ccatttggaa  2640
aacttaccag ttttttagatg tagatgtagt gaaaaacttc aagaatgaag cagagcaatt  2700
gagtattctt ttttaaatta ttaagccatg atttacaaaa acattacttt ctgtaattca  2760
caatacttgt tttaaaaaca tagtgtcttc attagtgtgc atctattaac tgttcatggt  2820
gttagagttg caaactttt agcaagaaaa tatggatttc ctcatttcag ttccttctgc  2880
agcctgtgaa tctccacaaa gtgttaccag tttacaaaaa taagtctttt tgccttaagt  2940
cattttggaa ataagtaata ctgcatctga ctctggtggc tgtattagct aggaaaggtt  3000
tgtaaatggt gtcagtgagg tggggaaagg aagtcttcct gtcacatatg caggttcgtt  3060
ttcattctag ggcagtgcca ggaagtatat tgatagcttt gtaggtacag gaaaaacatc  3120
atcattattt cctctgttca catttactgg tcttaattaa caggtaataa taatacatgt  3180 actttttagcc tgaaacctct tccacgccat gggtaacttg ggggagagaa gaatcctcca  3240
aacgatggag tagccagtgg taatacaaag cagggagaac agaaaggtag agttactaag  3300
gccttcagtg aacagaaagg agcagagagc aagattagat ctgagaagat gctctgggga  3360
ctgagcccac tgttgttggt gtcagggagg cttactggag ccacacctgc aggcgctgtg  3420
ttcaggcacc accttcctcc ttgagctttg cctgtctctt gccttatcag ttcttcctcc  3480
accaccctac acccccctcc ccccggcccc aagcccctgt gtctccttgt tacaattaag  3540
tttctggata ttgacttaag aactgttagg aagaggacta gaaaaggctt cccctgccta  3600
tcctctccga tcaccaaggt ggaagggagc tagtaggact cttccttgac acaccttgta  3660
gtctaaatgt tcggtattct attcaggact tacggtaact attatgaggg aggcatggct  3720
ttccaccgtc gggccaggaa gagcacctgt tgctgcaagc tcagtgaagt ggggcactcc  3780
cagacctgcc atgcagttta tcctctgaga atggaattgg aaatgaagac ctaaccagct  3840
attggtggga atgacggaac tggggattgc gatgattgat ctgggaacat ggctggattg  3900
tgatttaacc aagaatgctg atgttgaatt ctttgggcct agaatatact tgagaaagca  3960
ctagtggctt gtgttcaggg agaggagctg gcagttttta accacttctg tgggagccgt  4020
gttctaacct gtggaaagta ttgcaattct gtgagagtga ctctgcagag tcactgcacc  4080
atcaggcttg gccctgctgt gccttcagta cccagccagg ttctctgggt ccagggtgac  4140
tctccaaaga aattggcctt cagctggaga aaacattggg tggagactct cacttatgtt  4200
aatgcaatct tgaaatgact gaaaggtaga ttgccagcac agtgagtttc ccagcctgct  4260
```

-continued

```
cccccatcca cacttggaaa ttgagggagc atgaccgctc tctgacttca catgttaata    4320
gaggatcaga gcagagttgg gagtatattg gtcaggatca tagaaaagaa gacaaagctt    4380
gctcagccat gagatggcca ggtatccagt tttgttaact ctctttggga atttctttt     4440 cagcctgttt tttagcttag tgccattatg tcattttgat ttgtattcaa gtactcttca    4500
agtatctttg taatgaaggt ttggctactt gtataggtct gcctgcaggg tgaaaatgcc    4560
agtgtgaata ttctagctac caaacattgt ttttgttga aaaactgact ttctgttgtc     4620
tacctcaggc cttgtgcatt tgggttatct caagccagtc accacagagg gtctctaggg    4680
tctgcaaaat agaggccaaa tccagggacc aggccctaat aatagaagtt gtaccaaaat    4740
gcctgtggta cttgatggcc tgttggtcaa ataggaagta caagtgtgtg atgttagaac    4800
ctccctagtt gctgctatat caaacactgc acacttgaca agtgttttca ttccccgccc    4860
tctgacagaa caacattcct aattctttga aggcaaccag tgcaaaggct actacacttg    4920
tgtaatgata tttagcagat gcatacagga ctggatccca gggcactgtc agttcttccc    4980
tccctctcgt gctgctcagt ttgtcctctg ctcccatgta ggcctaaagt caccccactc    5040
cttagtgcct gcacctcacc acgatattga ggaagcacag gacatccaag ggtactctcc    5100
agtttggctg tggagacttg agcaagccct aaagtcccct gctccctgga cttctcctgg    5160
gttgtgcttt tttgggggca acatacttg gacaaagctg agctgacagc taatgtttat     5220
tagcctccta cctaagtcag tcactttgct aaattcttca cctgtggtaa ctcattttga    5280
ttgttataac atctcagcac cattattccc atttaatga tgaggaaact gagtcataga     5340
ggatacagac ttgcccaaag gagagccagg attttcacac ccctcctca agctgggcct     5400 gccctccaag tgcttgttat atacctccac gggtgtcagc ccagatgact cctcacccat    5460
ccaccacctg cagcttgaga tgttaactat tagagctcca ttctttggt tcaaaacgtt     5520 gatacttact tagatgttcc ctgagaggag tgtttatttc tgagtaaggg ctttgttga    5580 aagaggggt tagagagagc aagacagcac ttgagtgcac tggcaggaag cagagataag    5640
acttgaattt cagtttggta gaccaccttc tttagcagcc caacctgtag caaatctagt    5700
ttagcctgca tggcagggag agggattctc ttcccaccct caccatttgc aagtggcagg    5760
agctgagaat gccagtacga gagtgtagcc aaagtgagag gctgagagca aggagacat     5820 tttttttcagt tttgagtcga gtatccagac agaggcaaat cattttgttt aacttttat     5880 taaagtgtaa ctatagaaac acatcaatga tttttcacaa gtggagcacg tgcatacaat    5940
cggcacccca gaagccccc gtcagattcc cttccagtta actacctctc caagggaaac    6000
cactatcctg agttctaagc gcatagatta gttctgtctg gtttggggag atatataaat    6060
ggaattatgc attcttcgta tctggtttct tttcaccaat attatgtttg tgagattttt    6120
gttgcatgta tttgtacatg gattttcatt ctcatggttg tataatattt cattgtgtga    6180
ataaaccaca tactgtttat ctg                                           6203
```

```
<210> SEQ ID NO 4
<211> LENGTH: 597
<212> TYPE: PRT
<213> ORGANISM: Mus musculus

<400> SEQUENCE: 4

Met Ala Tyr Asn Lys Ile Pro Pro Arg Trp Leu Asn Cys Pro Arg Arg
 1               5                  10                  15

Gly Gln Pro Val Ala Gly Arg Phe Leu Pro Leu Lys Thr Met Leu Gly
             20                  25                  30
```

```
Pro Arg Tyr Asp Ser Gln Val Ala Glu Glu Asn Arg Phe His Pro Ser
         35                  40                  45

Met Leu Ser Asn Tyr Leu Lys Ser Leu Lys Val Lys Met Ser Leu Leu
     50                  55                  60

Val Asp Leu Thr Asn Thr Ser Arg Phe Tyr Arg Asn Asp Ile Glu
 65              70                  75                  80

Lys Glu Gly Ile Lys Tyr Ile Lys Leu Gln Cys Lys Gly His Gly Glu
                 85                  90                  95

Cys Pro Thr Thr Glu Asn Thr Glu Thr Phe Ile Arg Leu Cys Glu Arg
             100                 105                 110

Phe Asn Glu Arg Ser Pro Pro Glu Leu Ile Gly Val His Cys Thr His
         115                 120                 125

Gly Phe Asn Arg Thr Gly Phe Leu Ile Cys Ala Phe Leu Val Glu Lys
     130                 135                 140

Met Asp Trp Ser Ile Glu Ala Ala Val Ala Thr Phe Ala Gln Ala Arg
145                 150                 155                 160

Pro Pro Gly Ile Tyr Lys Gly Asp Tyr Leu Lys Glu Leu Phe Arg Arg
                 165                 170                 175

Tyr Gly Asp Ile Glu Glu Ala Pro Pro Pro Val Leu Pro Asp Trp
             180                 185                 190

Cys Phe Glu Asp Glu Asp Glu Glu Asp Glu Asp Glu Asp Gly Lys Lys
         195                 200                 205

Asp Ser Glu Pro Gly Ser Ser Ala Ser Phe Ser Lys Arg Arg Lys Glu
     210                 215                 220

Arg Leu Lys Leu Gly Ala Ile Phe Leu Glu Gly Ile Thr Val Lys Gly
225                 230                 235                 240

Val Thr Gln Val Thr Thr Gln Pro Lys Leu Gly Glu Val Gln Gln Lys
             245                 250                 255

Cys His Gln Phe Cys Gly Trp Glu Gly Ser Gly Phe Pro Gly Ala Gln
             260                 265                 270

Pro Val Ser Met Asp Lys Gln Asn Ile Arg Leu Leu Glu Gln Lys Pro
     275                 280                 285

Tyr Lys Val Ser Trp Lys Ala Asp Gly Thr Arg Tyr Met Met Leu Ile
     290                 295                 300

Asp Gly Thr Asn Glu Val Phe Met Ile Asp Arg Asp Asn Ser Val Phe
305                 310                 315                 320

His Val Ser Asn Leu Glu Phe Pro Phe Arg Lys Asp Leu Arg Met His
             325                 330                 335

Leu Ser Asn Thr Leu Leu Asp Gly Glu Met Ile Ile Asp Lys Val Asn
         340                 345                 350

Gly Gln Ala Val Pro Arg Tyr Leu Ile Tyr Asp Ile Ile Lys Phe Asn
     355                 360                 365

Ala Gln Pro Val Gly Asp Cys Asp Phe Asn Ile Arg Leu Gln Cys Ile
     370                 375                 380

Glu Arg Glu Ile Ile Ser Pro Arg His Glu Lys Met Lys Thr Gly Leu
385                 390                 395                 400

Ile Asp Lys Thr Gln Glu Pro Phe Ser Val Arg Pro Lys Gln Phe Phe
                 405                 410                 415

Asp Ile Asn Ile Ser Arg Lys Leu Leu Glu Gly Asn Phe Ala Lys Glu
             420                 425                 430

Val Ser His Glu Met Asp Gly Leu Ile Phe Gln Pro Ile Gly Lys Tyr
         435                 440                 445
```

-continued

```
Lys Pro Gly Arg Cys Asp Asp Ile Leu Lys Trp Lys Pro Pro Ser Leu
    450                 455                 460

Asn Ser Val Asp Phe Arg Leu Lys Ile Thr Arg Met Gly Gly Glu Gly
465                 470                 475                 480

Leu Leu Pro Gln Asn Val Gly Leu Leu Tyr Val Gly Gly Tyr Glu Arg
                485                 490                 495

Pro Phe Ala Gln Ile Lys Val Thr Lys Glu Leu Lys Gln Tyr Asp Asn
                500                 505                 510

Lys Ile Ile Glu Cys Lys Phe Glu Asn Asn Ser Trp Val Phe Met Arg
            515                 520                 525

Gln Arg Ile Asp Lys Ser Phe Pro Asn Ala Tyr Asn Thr Ala Met Ala
    530                 535                 540

Val Cys Asn Ser Ile Ser Asn Pro Val Thr Lys Glu Met Leu Phe Glu
545                 550                 555                 560

Phe Ile Asp Arg Cys Ala Ala Ala Gln Gly Gln Lys Arg Lys Tyr
                565                 570                 575

Pro Leu Asp Pro Asp Thr Glu Leu Met Pro Pro Pro Pro Lys Arg
                580                 585                 590

Leu His Arg Pro Thr
        595
```

<210> SEQ ID NO 5
<211> LENGTH: 597
<212> TYPE: PRT
<213> ORGANISM: Homo sapiens

<400> SEQUENCE: 5

```
Met Ala His Asn Lys Ile Pro Pro Arg Trp Leu Asn Cys Pro Arg Arg
1               5                   10                  15

Gly Gln Pro Val Ala Gly Arg Phe Leu Pro Leu Lys Thr Ile Leu Gly
                20                  25                  30

Pro Arg Tyr Asp Ser Gln Val Ala Glu Glu Asn Arg Phe His Pro Ser
            35                  40                  45

Met Leu Ser Asn Tyr Leu Lys Ser Leu Lys Val Lys Met Gly Leu Leu
    50                  55                  60

Val Asp Leu Thr Asn Thr Ser Arg Phe Tyr Asp Arg Asn Asp Ile Glu
65                  70                  75                  80

Lys Glu Gly Ile Lys Tyr Ile Lys Leu Gln Cys Lys Gly His Gly Glu
                85                  90                  95

Cys Pro Thr Thr Glu Asn Thr Glu Thr Phe Ile Arg Leu Cys Glu Arg
                100                 105                 110

Phe Asn Glu Arg Asn Pro Pro Glu Leu Ile Gly Val His Cys Thr His
            115                 120                 125

Gly Phe Asn Arg Thr Gly Phe Leu Ile Cys Ala Phe Leu Val Glu Lys
    130                 135                 140

Met Asp Trp Ser Ile Glu Ala Ala Val Ala Thr Phe Ala Gln Ala Arg
145                 150                 155                 160

Pro Pro Gly Ile Tyr Lys Gly Asp Tyr Leu Lys Glu Leu Phe Arg Arg
                165                 170                 175

Tyr Gly Asp Ile Glu Glu Ala Pro Pro Pro Leu Leu Pro Asp Trp
                180                 185                 190

Cys Phe Glu Asp Asp Glu Asp Glu Asp Glu Asp Gly Lys Lys
            195                 200                 205

Glu Ser Glu Pro Gly Ser Ser Ala Ser Phe Gly Lys Arg Arg Lys Glu
    210                 215                 220
```

```
Arg Leu Lys Leu Gly Ala Ile Phe Leu Glu Gly Val Thr Val Lys Gly
225                 230                 235                 240

Val Thr Gln Val Thr Thr Gln Pro Lys Leu Gly Glu Val Gln Gln Lys
            245                 250                 255

Cys His Gln Phe Cys Gly Trp Glu Gly Ser Gly Phe Pro Gly Ala Gln
            260                 265                 270

Pro Val Ser Met Asp Lys Gln Asn Ile Lys Leu Leu Asp Leu Lys Pro
            275                 280                 285

Tyr Lys Val Ser Trp Lys Ala Asp Gly Thr Arg Tyr Met Met Leu Ile
            290                 295                 300

Asp Gly Thr Asn Glu Val Phe Met Ile Asp Arg Asp Asn Ser Val Phe
305                 310                 315                 320

His Val Ser Asn Leu Glu Phe Pro Phe Arg Lys Asp Leu Arg Met His
            325                 330                 335

Leu Ser Asn Thr Leu Leu Asp Gly Glu Met Ile Ile Asp Arg Val Asn
            340                 345                 350

Gly Gln Ala Val Pro Arg Tyr Leu Ile Tyr Asp Ile Ile Lys Phe Asn
            355                 360                 365

Ser Gln Pro Val Gly Asp Cys Asp Phe Asn Val Arg Leu Gln Cys Ile
            370                 375                 380

Glu Arg Glu Ile Ile Ser Pro Arg His Glu Lys Met Lys Thr Gly Leu
385                 390                 395                 400

Ile Asp Lys Thr Gln Glu Pro Phe Ser Val Arg Asn Lys Pro Phe Phe
                405                 410                 415

Asp Ile Cys Thr Ser Arg Lys Leu Leu Glu Gly Asn Phe Ala Lys Glu
            420                 425                 430

Val Ser His Glu Met Asp Gly Leu Ile Phe Gln Pro Thr Gly Lys Tyr
            435                 440                 445

Lys Pro Gly Arg Cys Asp Asp Ile Leu Lys Trp Lys Pro Pro Ser Leu
            450                 455                 460

Asn Ser Val Asp Phe Arg Leu Lys Ile Thr Arg Met Gly Gly Glu Gly
465                 470                 475                 480

Leu Leu Pro Pro Asn Val Gly Leu Leu Tyr Val Gly Gly Tyr Glu Arg
                485                 490                 495

Pro Phe Ala Gln Ile Lys Val Thr Lys Glu Leu Lys Gln Tyr Asp Asn
            500                 505                 510

Lys Ile Ile Glu Cys Lys Phe Glu Asn Asn Ser Trp Val Phe Met Arg
            515                 520                 525

Gln Arg Thr Asp Lys Ser Phe Pro Asn Ala Tyr Asn Thr Ala Met Ala
            530                 535                 540

Val Cys Asn Ser Ile Ser Asn Pro Val Thr Lys Glu Met Leu Phe Glu
545                 550                 555                 560

Phe Ile Asp Arg Cys Thr Ala Ala Ser Gln Gly Lys Arg Lys His
            565                 570                 575

His Leu Asp Pro Asp Thr Glu Leu Met Pro Pro Pro Pro Lys Arg
            580                 585                 590

Pro Arg Pro Leu Thr
        595

<210> SEQ ID NO 6
<211> LENGTH: 476
<212> TYPE: PRT
<213> ORGANISM: Homo sapiens
```

-continued

<400> SEQUENCE: 6

Met Ala Asn Ser Ala Lys Ala Glu Glu Tyr Glu Lys Met Ser Leu Glu
1               5                   10                  15

Gln Ala Lys Ala Ser Val Asn Ser Glu Thr Gly Ser Ser Phe Asn Ile
            20                  25                  30

Asn Glu Asn Thr Thr Ala Ser Gly Thr Gly Leu Ser Glu Lys Thr Ser
        35                  40                  45

Val Cys Arg Gln Val Asp Ile Ala Arg Lys Lys Glu Phe Glu Asp
    50                  55                  60

Asp Leu Val Lys Glu Ser Ser Cys Gly Lys Asp Thr Pro Ser Lys
65                  70                  75                  80

Lys Arg Lys Leu Asp Pro Glu Ile Val Pro Glu Glu Lys Asp Cys Gly
            85                  90                  95

Asp Ala Glu Gly Asn Ser Lys Lys Arg Lys Glu Thr Glu Asp Val
            100                 105                 110

Pro Lys Asp Lys Ser Ser Thr Gly Asp Gly Thr Gln Asn Lys Arg Lys
            115                 120                 125

Ile Ala Leu Glu Asp Val Pro Glu Lys Gln Lys Asn Leu Glu Glu Gly
130                 135                 140

His Ser Ser Thr Val Ala Ala His Tyr Asn Glu Leu Gln Glu Val Gly
145                 150                 155                 160

Leu Glu Lys Arg Ser Gln Ser Arg Ile Phe Tyr Leu Arg Asn Phe Asn
            165                 170                 175

Asn Trp Met Lys Ser Val Leu Ile Gly Glu Phe Leu Glu Lys Val Arg
            180                 185                 190

Gln Lys Lys Lys Arg Asp Ile Thr Val Leu Asp Leu Gly Cys Gly Lys
            195                 200                 205

Gly Gly Asp Leu Leu Lys Trp Lys Lys Gly Arg Ile Asn Lys Leu Val
210                 215                 220

Cys Thr Asp Ile Ala Asp Val Ser Val Lys Gln Cys Gln Gln Arg Tyr
225                 230                 235                 240

Glu Asp Met Lys Asn Arg Arg Asp Ser Glu Tyr Ile Phe Ser Ala Glu
            245                 250                 255

Phe Ile Thr Ala Asp Ser Ser Lys Glu Leu Leu Ile Asp Lys Phe Arg
            260                 265                 270

Asp Pro Gln Met Cys Phe Asp Ile Cys Ser Cys Gln Phe Val Cys His
            275                 280                 285

Tyr Ser Phe Glu Ser Tyr Glu Gln Ala Asp Met Met Leu Arg Asn Ala
290                 295                 300

Cys Glu Arg Leu Ser Pro Gly Gly Tyr Phe Ile Gly Thr Thr Pro Asn
305                 310                 315                 320

Ser Phe Glu Leu Ile Arg Arg Leu Glu Ala Ser Glu Thr Glu Ser Phe
            325                 330                 335

Gly Asn Glu Ile Tyr Thr Val Lys Phe Gln Lys Lys Gly Asp Tyr Pro
            340                 345                 350

Leu Phe Gly Cys Lys Tyr Asp Phe Asn Leu Glu Gly Val Val Asp Val
            355                 360                 365

Pro Glu Phe Leu Val Tyr Phe Pro Leu Leu Asn Glu Met Ala Lys Lys
370                 375                 380

Tyr Asn Met Lys Leu Val Tyr Lys Lys Thr Phe Leu Glu Phe Tyr Glu
385                 390                 395                 400

Glu Lys Ile Lys Asn Asn Glu Asn Lys Met Leu Leu Lys Arg Met Gln
            405                 410                 415

Ala Leu Glu Pro Tyr Pro Ala Asn Glu Ser Ser Lys Leu Val Ser Glu
          420                 425                 430

Lys Val Asp Asp Tyr Glu His Ala Ala Lys Tyr Met Lys Asn Ser Gln
          435                 440                 445

Val Arg Leu Pro Leu Gly Thr Leu Ser Lys Ser Glu Trp Glu Ala Thr
      450                 455                 460

Ser Ile Tyr Leu Val Phe Ala Phe Glu Lys Gln Gln
465                 470                 475

<210> SEQ ID NO 7
<211> LENGTH: 15
<212> TYPE: PRT
<213> ORGANISM: Unknown
<220> FEATURE:
<223> OTHER INFORMATION: Description of Unknown Organism: peptide

<400> SEQUENCE: 7

Gly Val His Cys Thr His Gly Phe Asn Arg Thr Gly Phe Leu Ile
 1               5                  10                  15

<210> SEQ ID NO 8
<211> LENGTH: 26
<212> TYPE: DNA
<213> ORGANISM: Unknown
<220> FEATURE:
<223> OTHER INFORMATION: Description of Unknown Organism: primer

<400> SEQUENCE: 8
gggcggctgc tgcacatctg tcaatg                                          26

<210> SEQ ID NO 9
<211> LENGTH: 27
<212> TYPE: DNA
<213> ORGANISM: Unknown
<220> FEATURE:
<223> OTHER INFORMATION: Description of Unknown Organism: primer

<400> SEQUENCE: 9
cccaaatgcc tacaacacag ccatggc                                         27

<210> SEQ ID NO 10
<211> LENGTH: 10
<212> TYPE: PRT
<213> ORGANISM: Unknown
<220> FEATURE:
<223> OTHER INFORMATION: Description of Unknown Organism: peptide

<400> SEQUENCE: 10

Gly Thr Leu Ser Lys Ser Glu Trp Glu Ala
 1               5                  10

<210> SEQ ID NO 11
<211> LENGTH: 32
<212> TYPE: DNA
<213> ORGANISM: Unknown
<220> FEATURE:
<223> OTHER INFORMATION: Description of Unknown Organism: primer

<400> SEQUENCE: 11
ctgcagatgt caaaacacat ttgtgggtca cg                                   32

<210> SEQ ID NO 12
<211> LENGTH: 10
<212> TYPE: PRT

-continued

```
<213> ORGANISM: Unknown
<220> FEATURE:
<223> OTHER INFORMATION: Description of Unknown Organism: peptide

<400> SEQUENCE: 12

Gly Thr Leu Ser Lys Ser Glu Trp Glu Ala
 1               5                  10

<210> SEQ ID NO 13
<211> LENGTH: 29
<212> TYPE: DNA
<213> ORGANISM: Unknown
<220> FEATURE:
<223> OTHER INFORMATION: Description of Unknown Organism: primer

<400> SEQUENCE: 13
gcttcccatt cagatttaga aagagttcc                                      29

<210> SEQ ID NO 14
<211> LENGTH: 29
<212> TYPE: DNA
<213> ORGANISM: Unknown
<220> FEATURE:
<223> OTHER INFORMATION: Description of Unknown Organism: primer

<400> SEQUENCE: 14
gcttctggga ctgggctttg tgaaaagac                                      29

<210> SEQ ID NO 15
<211> LENGTH: 33
<212> TYPE: DNA
<213> ORGANISM: Unknown
<220> FEATURE:
<223> OTHER INFORMATION: Description of Unknown Organism: primer

<400> SEQUENCE: 15
ggatccccta agaactttaa taattggatg aaa                                 33

<210> SEQ ID NO 16
<211> LENGTH: 32
<212> TYPE: DNA
<213> ORGANISM: Unknown
<220> FEATURE:
<223> OTHER INFORMATION: Description of Unknown Organism: primer

<400> SEQUENCE: 16
ggattcgttt ctcagcatca tgtcagcctg ct                                  32

<210> SEQ ID NO 17
<211> LENGTH: 30
<212> TYPE: DNA
<213> ORGANISM: Unknown
<220> FEATURE:
<223> OTHER INFORMATION: Description of Unknown Organism: primer

<400> SEQUENCE: 17
gcggatccat ggcaaattct gcaaaagcag                                     30

<210> SEQ ID NO 18
<211> LENGTH: 29
<212> TYPE: DNA
<213> ORGANISM: Unknown
<220> FEATURE:
<223> OTHER INFORMATION: Description of Unknown Organism: primer

<400> SEQUENCE: 18
```

```
                                     -continued cgctcgagtc actgctgttt ctcaaaggc                                     29

<210> SEQ ID NO 19
<211> LENGTH: 30
<212> TYPE: DNA
<213> ORGANISM: Unknown
<220> FEATURE:
<223> OTHER INFORMATION: Description of Unknown Organism: primer

<400> SEQUENCE: 19
cgctcgagtc atagtttcat attgtacttc                                    30
```

MRNA CAPPING ENZYMES AND USES THEREOF

GOVERNMENTAL SUPPORT

Certain of the work leading to the present invention has been supported by NIH GM 37129, 797-033, and the New Jersey Commission on Cancer Research and the New Jersey Commission on Science and Technology. The government may have certain rights in the invention.

Throughout this application, various publications are referenced by author and year and/or by number. Full citations for these publications may be found listed at the end of the specification immediately following the Sequence Listing and preceding the Claims. The disclosures of these publications in their entireties are hereby incorporated by reference into this application in order to more fully describe the state of the art. The Sequence Listing is provided following the list of references and before the Claims.

FIELD OF THE INVENTION

The present invention relates to RNA polymerases, and particularly to enzymes involved in adding the cap structure to mRNA transcripts. The present invention further relates to transcription and translation of mRNA.

BACKGROUND OF THE INVENTION

Eukaryotic mRNAs contain a 5'-terminal cap, $m^7$GpppN (1). This important modification of RNA polymerase II (pol II) transcripts occurs soon after they attain a chain length of 25–30 nucleotides (2–4). At this stage in transcription the C-terminal domain (CTD) of the pol II largest subunit is hyperphosphorylated (5, 6), and capping enzyme (CE) then binds to it (7–9). In mammals, CE is a bifunctional protein consisting of N-terminal RNA 5'-triphosphatase and C-terminal guanylyltransferase domains (7, 10). The combined effect of these activities on nascent pre-mRNAs is the conversion of 5'-terminal pppN to GpppN. Subsequent N7-methylation of GpppN 5' ends to form $m^7$GpppN caps is catalyzed by RNA (guanine-7-) methyltransferase (1, 11, 12). The 7-methylguanosine ($m^7$G) moiety of the cap is a key feature in several aspects of RNA metabolism including transcript stability (13, 14), processing (15–17), transport to the cytoplasm (18, 19) and initiation of translation (1, 20).

Several functions of the cap structure are mediated by a family of cap-binding protein complexes that specifically recognize $m^7$GpppN (19, 21). For example, in the nucleus, a cap-binding protein complex facilitates pre-mRNA splicing accuracy and efficiency and possibly nuclear export (19). In the cytoplasm, the heterotrimeric initiation factor eIF4F, which includes the cap-binding subunit eIF4E, promotes ribosome binding and translation initiation (21, 22). Although capping stabilizes mRNAs (13, 14), cap $m^7$G is also recognized by the yeast decapping enzyme (23), and loss of the blocked 5' end leads to 5'→3' exonucleolytic degradation (13, 24). Consistent with the multiple effects of cap on gene expression, the RNA (guanine-7-) methyltransferase, like the RNA 5'-triphosphatase (25) and guanylyltransferase (26), is essential for viability in yeast (27).

SUMMARY OF THE INVENTION

The present invention provides an isolated nucleic acid encoding a mammalian capping enzyme. The present invention further provides an isolated nucleic acid encoding a mammalian (Guanine-7-) methyltransferase enzyme.

The present invention also provides an isolated mammalian capping enzyme protein or subunit thereof. In addition the present invention provides an isolated mammalian (Guanine-7-) methyltransferase enzyme protein or portion thereof.

It is an object of the present invention to provide a method for catalyzing formation of RNA 5'-terminal GpppN cap complex.

It is a further object of the present invention to provide a method for coupled formation of RNA 5'-terminal GpppN cap complex and translation of the RNA 5'-terminal GpppN cap complex in a cell-free extract.

It is a still further object of the present invention to provide a method for coupling RNA transcription and catalyzed formation of RNA 5'-terminal GpppN cap complex and translation of the RNA 5'-terminal GpppN cap complex in a cell-free extract comprising.

It is also an object of the present invention to provide a method for catalyzing formation of a methylated RNA 5'-terminal GpppN cap complex.

It is an even further object of the present invention to provide a kit for catalyzing formation of a methylated RNA 5'-terminal GpppN cap complex.

It is also a further object of the present invention to provide a kit for producing protein from a DNA template through coupled transcription, catalyzed formation of RNA 5'-terminal GpppN cap complex and translation.

Even still further it is an object of the present invention to provide a kit for producing protein from an uncapped RNA template through coupled catalyzed formation of RNA 5'-terminal GpppN cap complex and translation.

It is yet another object of the present invention to provide a mammalian RNA polymerase II/capping enzyme composition comprising RNA polymerase II and the provided mammalian capping enzyme protein.

Finally, it is an object of the present invention to provide a method for inhibiting degradation of an RNA transcript comprising contacting the RNA transcript with the provided mammalian capping enzyme protein under conditions permissive to the formation of a complex between the RNA transcript and the mammalian capping enzyme protein.

The present invention also contemplates using the provided nucleic acids, plasmids vectors and cells in an complementation assays in order to identify, screen, correct, treat and/or monitor a genetic defect in the capping pathway.

BRIEF DESCRIPTION OF THE FIGURES

FIGS. 1A–1B. Mouse capping enzyme (MCE) and human capping enzyme (HCE) cDNA clones. FIG. 1A. Schematic diagram of the ORFs (1,794 bp, solid bars), relative sizes of the untranslated regions, and the sequences and positions of initiation sites and polyadenylation signals. FIG. 1B. (1B-1 and 1-B2) Predicted amino acid sequences of the mouse and human enzymes. Residues that are identical (95% of total) are omitted from the human sequence.

FIG. 2. (A, 2B, and 2C) Sequence alignments of cellular mRNA guanylyltransferases. The deduced amino acid sequences of the C-terminal regions of the mouse and human enzymes (residues 232–597) are compared with C. elegans CEL-1 (residues 238–573; ref 19) and to the nearly full-length S. pombe (13) and S. cerevisiae (9) guanylyltransferase subunits of capping enzyme. Dark background indicates regions of sequence identity; the active site motif, including Lys-294, in the mammalian enzymes is bracketed. The amino acid sequence of mouse CE is shown in Seq.ID.No.: 4. The amino acid sequence of human CE is shown in Seq.ID.No.: 5.

FIG. 3A. Poly(A)+ RNAs prepared from mouse adult tissues (Left) and embryos at the indicated days of gestation (Right) were probed with a mouse EST as described in Materials and Methods. FIG. 3B. Human adult tissue poly(A)+ RNAs were probed with the same EST and a human β-actin cDNA. Positions of marker RNAs and hybridized transcripts (arrows) are indicated.

FIGS. 4A–4B. In vitro synthesis and specific immunoprecipitation of MCEs. FIG. 4A. 35S-methionine-labeled proteins were synthesized in vitro by using luciferase (Luc) cDNA (lane 1) or cDNAs for wild type (lane 2), mutant (lane 3), and C-terminal fragment (Δ210, lane 4) of MCE. Products were analyzed by SDS/PAGE and autoradiography. FIG. 4B. Products shown in FIG. 4A were immunoprecipitated with α MCE and analyzed by SDS/PAGE and autoradiography.

FIG. 5A. In vitro translated and immunoprecipitated proteins were incubated with $\alpha[^{32}P]GTP$ as described in Materials and Methods and analyzed by SDS/PAGE and autoradiography. Lane 1, no added DNA; lanes 2–5, products synthesized with cDNA templates for full-length MCE, C-terminal fragment (Δ210), and mutants K294A and K290A, respectively. Mouse L cell nuclear extract (lane 6) and partially purified HeLa cell capping enzyme (lane 7) were immunoprecipitated with αMCE and then incubated with $\alpha[^{32}P]GTP$. Proteins were analyzed by SDS/PAGE and autoradiography. FIG. 5B. 5'-Terminal guanylylation of T7 transcripts was assayed by incubating the RNA with $\alpha[^{32}P]GTP$ and immunoprecipitates of in vitro synthesized wild-type (lane 2) or K294A mutant (lane 3) MCE or vaccinia virus capping enzyme (VCE, lane 4). (C) Cap formation on the radiolabeled RNAs shown in FIG. 5B was verified by digestion with P1 nuclease followed by alkaline phosphatase and TLC analysis of the digests with authentic GpppG and GppppG as markers.

FIG. 8A. A HeLa cell protein fraction containing approximately equal amounts of the phosphorylated (pol IIo) and unphosphorylated (pol IIa) forms of pol II (lane 1) was mixed with αMCE-protein A beads in the presence or absence of affinity-purified HeLa capping enzyme (HCE, lane 2). Immunoprecipitates (lane 3 and 4) were extensively washed and loaded onto a 5–20% gradient SDS-polyacrylamide gel with the input (10%, lanes 1 and 2) for Western blot analysis. Immunoblots were developed for the CTD of the largest subunit of pol II (Upper) or capping enzyme (Lower). FIG. 8B. The carboxy-terminal domain of capping enzyme is sufficient to mediate direct and selective interaction with the phosphorylated form of pol II. The HeLa protein fraction containing the two forms of pol II (lane 1) was mixed with antihexahistidine tag antibody (α6×His)-protein G beads in the presence or absence of purified, recombinant hexa-histidine tagged carboxy-terminal domain of MCE Δ210. Immunoprecipitates (lanes 2 and 3) were extensively washed and loaded onto a 5–20% gradient SDS-polyacrylamide gel with the input (10%, lane 1) for Western blot analysis. Immunoblots were developed for the CTD of the largest subunit of pol II (Upper) or MCE (Lower).

FIG. 9. (9A, 9B and 9C) Sequence alignment of cellular RNA (guanine-7-) methyltransferases. Deduced amino acid sequences of the human (Seq.ID.No.: 6), S. cerevisiae, C. elegans and Drosophila enzymes are compared. Dark background indicates regions of identity. Motifs I, III and X are indicated.

FIGS. 11A–11B. RNA (guanine-7) methyltransferase activity of recombinant hMet. FIG. 11A. T7 polymerase run-off transcripts containing $G^{32}pppG$ 5' ends were incubated as described in Materials and Methods with 2.5 mg of bacterially expressed, purified GST-hMet bound to glutathione beads (lane 1) and the same amount of GST-hMet in solution (lane 2). Purified GST (2.5mg) (lane 3) and vaccinia virus CE (3.4 units, lane 4) were included as controls. P1 nuclease digested samples and the indicated standards (Pharmacia) were analyzed by TLC and autoradiography. FIG. 11B. 6×His-tagged full length hMet (1 mg, lane 1) and hMet 1–389 (1 mg, lane 2) were immobilized on protein A beads using monoclonal antibody to 6×His (CLONTECH) and assayed for methyltransferase activity as in panel A. Vaccinia virus CE (3.4 units) was assayed as a control (lane 3).

DETAILED DESCRIPTION

Figure 3A:
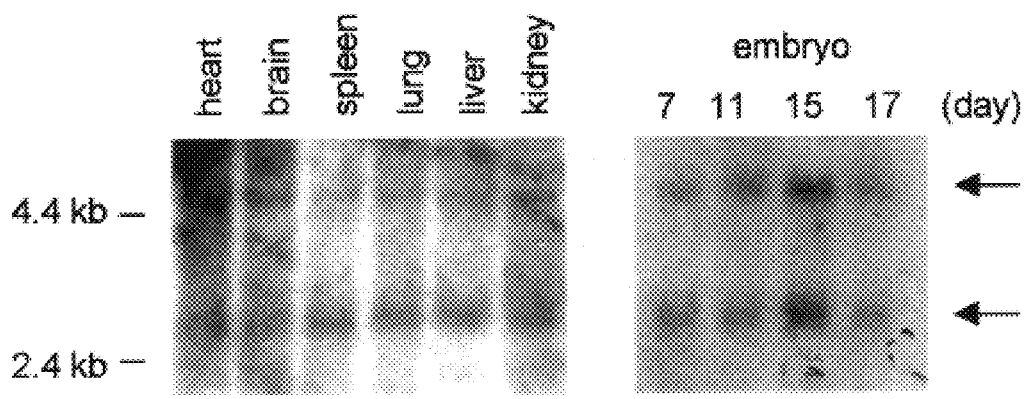
FIGS. 3A–3B. Expression of capping enzyme transcripts in vivo.

The present invention provides an isolated nucleic acid encoding a mammalian capping enzyme. In one embodiment of this invention, the isolated nucleic acid is encoding the N-terminal portion of the mammalian capping enzyme or a portion thereof. In another embodiment of this invention, the isolated nucleic acid is encoding the C-terminal portion of the mammalian capping enzyme or a portion thereof. An embodiment of this invention provides an isolated mammalian capping enzyme nucleic acid having the following characteristics: (a) the ability to catalyze formation of an RNA 5'-terminal GpppN cap complex, wherein N is any nucleotide, nucleoside or analog thereof, and (b) the ability to hybridize under standard hybridization conditions to the sequence shown in Seq.ID.No.: 1. The present invention further provides an isolated nucleic acid encoding a mammalian (Guanine-7-) methyltransferase enzyme. An embodiment of this invention provides an isolated nucleic acid encoding a mammalian (Guanine-7-) methyltransferase enzyme having the following characteristics: (a) the ability to catalyze formation of a methylated RNA 5'-terminal GpppN cap complex, wherein N is any nucleotide, nucleoside or analog thereof, and (b) the ability to hybridize under standard hybridization conditions to the sequence shown in Seq.ID.No.: 3.

According to an embodiment of the present invention the isolated nucleic acid is selected from the group consisting of mouse, human, rabbit, rat, dog, goat and monkey. In yet another embodiment of the present invention the isolated nucleic acid comprises the sequence shown in Seq.ID.No.: 1, Seq.ID.No.: 2, Seq.ID.No.: 3 or a portion thereof. According to still another embodiment of this invention, the nucleic acid is DNA or RNA. According to yet still another embodiment of this invention, the nucleic acid is cDNA. Another embodiment of the present invention is vector comprising the provided nucleic acid. According to a further embodiment of this invention, the vector comprises viral or plasmid DNA. A still further embodiment of this invention is an expression vector comprising the provided nucleic acid and a regulatory element. An even further embodiment of this invention is a host vector system which comprises the provided expression vector in a suitable host. One embodiment of this invention is a vector comprising cDNA encoding mammalian capping enzyme (ATCC Accession No.: 203150)(mouse). Another embodiment of this invention is a vector comprising cDNA encoding mammalian capping enzyme (ATCC Accession No.: 203149)(human). Another embodiment of this invention is a vector comprising cDNA encoding mammalian capping enzyme mutant K294A (ATCC Accession No.: 203152). Still another embodiment of this invention is a vector comprising cDNA encoding mammalian (Guanine-7-) methyltransferase enzyme (ATCC Accession No.: 203151). According to another embodiment of this invention the suitable host is selected from the group consisting of a bacterial cell, a eukaryotic cell, a mammalian cell and an insect cell.

The present invention also provides an isolated mammalian capping enzyme protein or subunit thereof. In one embodiment of this invention, the isolated protein is the N-terminal portion of the mammalian capping enzyme or a portion thereof. In another embodiment of this invention, the isolated protein is the C-terminal portion of the mammalian capping enzyme or a portion thereof. In addition the present invention provides an isolated mammalian (Guanine-7-) methyltransferase enzyme protein or portion thereof. According to one embodiment of the present invention, the mammalian capping enzyme protein comprises the sequence shown by Seq. ID.No: 4, Seq. ID.No: 5 or a portion thereof. According to still another embodiment of this invention, the isolated mammalian (Guanine-7-) methyltransferase enzyme protein comprises the sequence shown by Seq. ID.No: 6 or a portion thereof.

The present invention, in an embodiment, further provides an isolated mammalian capping enzyme protein or subunit thereof having the ability to catalyze formation of an RNA-5'terminal GpppN cap complex, wherein N is any nucleotide, nucleoside or analog thereof. Variants, including allelic variants, muteins, analogs and fragments capable of functioning as the provided mammalian capping enzyme are also contemplated by this invention. In a preferred embodiment, N is G. Also, the present invention provides in another embodiment, an isolated mammalian (Guanine-7-) methyltransferase enzyme protein or subunit thereof, having the ability to catalyze formation of a methylated RNA 5' terminal GpppN cap complex, wherein N is any nucleotide, nucleoside, or analog thereof. Variants, including allelic variants, muteins, analogs and fragments capable of functioning as the provided mammalian methyl transferase enzyme are also contemplated by this invention. In a preferred embodiment, N is G. The present invention further contemplates fusion proteins which are well known and described in the art.

The present invention further provides a method for catalyzing formation of RNA 5'-terminal GpppG cap complex, comprising the step of contacting an RNA transcript with the mammalian capping enzyme protein under conditions permissive to the formation of the RNA 5'-terminal GpppN cap complex. One embodiment of this invention, is further comprising contacting the complex with the provided mammalian (Guanine-7-) methyltransferase enzyme.

The present invention still further provides a method for coupled formation of RNA 5'-terminal GpppN cap complex and translation of the RNA 5'-terminal GpppN cap complex in a cell-free extract comprising: (a) contacting an RNA transcript with the mammalian cap enzyme protein under conditions permissive to the formation of RNA 5'-terminal GpppN cap complex, thereby forming a capped RNA transcript; and (b) incubating the capped RNA transcript formed in step (a) with the cell-free extract under conditions permissive to protein translation. One embodiment of this invention, is further comprising contacting the complex with the provided mammalian (Guanine-7-) methyltransferase enzyme.

The present invention further still provides a method for catalyzing formation of RNA 5'-terminal GpppN cap complex, comprising the step of contacting an RNA transcript with the provided nucleic acid encoding mammalian capping enzyme under conditions permissive to the formation of the RNA 5'-terminal GpppN cap complex.

Additionally the present invention provides a method for coupling catalyzed formation of RNA 5'-terminal GpppN cap complex and translation of the RNA 5'-terminal GpppN cap complex in a cell-free extract comprising: (a) contacting an RNA transcript with the provided nucleic acid encoding mammalian capping enzyme under conditions permissive to the formation of RNA 5'-terminal GpppN cap complex, thereby forming a capped RNA transcript; and (b) incubating the capped RNA transcript formed in step (a) with the cell-free extract under conditions permissive to protein translation. An embodiment of this invention is further comprising contacting the complex with the provided nucleic acid encoding mammalian (Guanine-7-) methyltransferase enzyme.

The present invention even still further provides a method for coupling RNA transcription and catalyzed formation of RNA 5'-terminal GpppN cap complex and translation of the RNA 5'-terminal GpppN cap complex in a cell-free extract comprising: (a) contacting a DNA template with RNA polymerase in a reaction buffer under conditions permissive to the formation of an RNA transcript; (b) contacting the RNA transcript with the provided mammalian capping enzyme protein under conditions permissive to the formation of RNA 5'-terminal GpppN cap complex, thereby forming a capped RNA transcript; and (c) incubating the capped RNA transcript formed in step (b) with the cell-free extract under conditions permissive to protein translation.

Also, the present invention provides a method for catalyzing formation of a methylated RNA 5'-terminal GpppN cap complex comprising contacting an RNA transcript with the provided mammalian (Guanine-7-) methyltransferase enzyme under conditions permissive to the formation methylated RNA 5'-terminal GpppN cap complex. One embodiment of this invention is further comprising adding S-adenosylmethionine to the RNA transcript. According to another embodiment of this invention, step (b) comprises contacting the RNA transcript with the provided nucleic acid encoding mammalian capping enzyme under conditions permissive to the formation of RNA 5'-terminal GpppN cap complex, thereby forming a capped RNA transcript. Another embodiment of this invention is step (b) further comprising contacting the capped RNA transcript with the provided mammalian (Guanine-7-) methyltransferase enzyme protein. Still another embodiment of this invention is step (b) further comprising contacting the capped RNA transcript with the provided nucleic acid encoding mammalian (Guanine-7-) methyltransferase enzyme.

Further still, the present invention provides a method for catalyzing formation of a methylated RNA 5'-terminal GpppN cap complex comprising contacting an RNA transcript with the provided nucleic acid encoding mammalian (Guanine-7-) methyltransferase enzyme under conditions permissive to the formation methylated RNA 5'-terminal GpppN cap complex, thereby forming a 7-methyl G capped RNA.

An embodiment of the present invention is further comprising adding at least one selected from the group consisting of ribonuclease inhibitor, an amino acid mixture, ATP, S-adenosylmethionine, magnesium salt, and nucleotide mixture.

Even further still, the present invention also provides a kit for catalyzing formation of a methylated RNA 5'-terminal GpppN cap complex comprising the provided nucleic acid encoding mammalian capping enzyme or a portion thereof. Also, the present invention provides a kit for catalyzing formation of a methylated RNA 5'-terminal GpppN cap complex comprising the provided mammalian (Guanine-7-) methyltransferase enzyme protein or a portion thereof.

Further also, the present invention provides a kit for producing protein from a DNA template through coupled transcription, catalyzed formation of RNA 5'-terminal GpppN cap complex and translation comprising (a) the provided nucleic acid encoding mammalian capping enzyme or a portion thereof; (b) eukaryotic, cell-free cell extract selected from the group consisting of plant and animal cells; (c) ribonucleotide triphosphates; and (d) RNA polymerase. According to an embodiment of this invention, the provided nucleic acid encoding mammalian capping enzyme further comprises an expression vector and regulatory elements.

Also further, the present invention provides a kit for producing protein from an uncapped RNA template through coupled catalyzed formation of RNA 5'-terminal GpppN cap complex and translation, wherein the kit comprises: (a) the provided nucleic acid encoding mammalian capping enzyme; and (b) eukaryotic, cell-free extract of cells selected from the group consisting of plant and animal cells. In a preferred embodiment, the cell-free extract is rabbit reticulocyte lysate. In another embodiment the extract is wheat germ extract.

One embodiment of the present invention is further comprising at least one selected from the group consisting of the provided nucleic acid encoding mammalian (Guanine-7-) methyltransferase enzyme the protein, RNA polymerase, a ribonucleotide triphosphate mixture, a ribonuclease inhibitor, an amino acid mixture, ATP, S-adenosylmethionine, magnesium salt, a DNA template, a capped RNA transcript, and an uncapped RNA transcript.

According to a preferred embodiment of this invention the extract is selected from the group consisting of rabbit reticulocyte lysate and wheat germ extract.

The present invention additionally provides a mammalian RNA polymerase II/capping enzyme composition comprising RNA polymerase II and the provided mammalian capping enzyme protein. One embodiment of this invention is further comprising the provided mammalian (Guanine-7-) methyltransferase enzyme protein.

Finally, the present invention provides a method for inhibiting degradation of an RNA transcript comprising contacting the RNA transcript with the provided mammalian capping enzyme protein under conditions permissive to the formation of a complex between the RNA transcript and the mammalian capping enzyme protein.

Additionally, the present invention contemplates using the provided nucleic acids, plasmids vectors and cells in an complementation assays in order to identify, screen, correct and/or monitor a genetic defect in the capping pathway.

As used herein, in the term "GpppN," N is any nucleotide, nucleoside or analog thereof, most preferably G.

As used herein, the term "pol II" means RNA polymerase II; the term "CTD" means C-terminal domain; the term "EST" means expressed sequence tag; the term "MCE" means mouse capping enzyme, and the term "HCE" means human capping enzyme. As used herein, the term, "N-terminal portion" means the about 50% amino acids or portion thereof nearest to the amino terminus of the protein. The term "C-terminal portion" means the about 50% of the amino acids or portion thereof nearest the carboxy terminus of the protein.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994)]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

A "replicon" is any genetic element (e.g., plasmid, chromosome, virus) that functions as an autonomous unit of DNA replication in vivo; i.e., capable of replication under its own control. A "vector" is a replicon, such as plasmid, phage or cosmid, to which another DNA segment may be attached so as to bring about the replication of the attached segment. An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. Transcriptional and translational control sequences are DNA regulatory sequences, such as promoters, enhancers, polyadenylation signals, terminators, and the like, that provide for the expression of a coding sequence in a host cell.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used generally herein, such as in referring to probes prepared and used in the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

"Degenerate" means that a different three-letter codon is used to specify a particular amino acid. Two amino acid sequences are "substantially homologous" when at least about 70% of the amino acid residues (preferably at least about 80%, and most preferably at least about 90 or 95%) are identical, or represent conservative substitutions. Thus, a derivative of the invention can include, but is not limited to, those containing, a s a primary amino acid sequence, all or part of the amino acid sequence of the provided proteins including altered sequences in which functionally equivalent amino acid residues are substituted for residues within the sequence resulting in a conservative amino acid substitution. Such substitutions are defined herein as conservative substitutions.

For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic)amino acids include alanine, leucine, isoleucine, valine, proline, pheylalanine, tryptophan and methionine. Amino acids containing aromatic ring structures are phenylalanine, trptophan, and tyrosine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Such alterations will not be expected to significantly affect apparent molecular weight as determined by polyacrylamide gel electrophoresis, or isoelectric point.

Particular preferred conservative substitutions are:

-Lys for Arg and vice versa such that a positive charge may be maintained;

-Glu for Asp and vice versa such that a negative charge may be maintained;

-Ser for Thr such that a free —OH can be maintained; and

-Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. Pro may be introduced because of its particularly planar structure, which induces beta turns in the protein's structure.

A "heterologous nucleotide sequence" as used herein is a nucleotide sequence that is added to a nucleotide sequence of the present invention by recombinant methods to form a nucleic acid which is not naturally formed in nature. Such nucleic acids can encode chimeric and/or fusion proteins. Thus, the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed. In still another such embodiment the heterologous nucleotide can function as a means of detecting a nucleotide sequence of the present invention. A heterologous nucleotide sequence can comprise non-coding sequences including restriction sites, regulatory sites, promoters and the like.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10–20° C. below the predicted or determined $T_m$ with washes of higher stringency, if desired.

It is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly with regard to potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

A general method for site-specific incorporation of unnatural amino acids into proteins is described in Christopher J. Noren, Spencer J. Anthony-Cahill, Michael C. Griffith, Peter G. Schultz, *Science*, 244:182–188 (April 1989). This method may be used to create analogs with unnatural amino acids.

Addition of a 5'-terminal cap is an important early event in mRNA formation (Shatkin, 1976). This structural hallmark of most eukaryotic mRNAs enhances splicing (Edery and Sonenberg, 1985; Konarska, et al., 1984; Krainer, et al., 1984), transport (Hamm and Mattaj, 1990), translation (Shatkin, 1985) and stability (Furuichi, et al., 1977; Murthy, et al., 1991; Shimotohno, et al., 1977). In addition, mRNA capping is essential for viabiltiy (Shibagaki, et al., 1992).

Caps are formed on nascent nuclear pre-mRNAs by conversion of 5'-tri to 5'diphosphate ends, followed by addition of GMP and methylation (Mizumoto and Kaziro, 1987; Shatkin, 1976). The guanylyltransfer reaction characterized in various systems involves formation of an active enzyme intermediate containing GMP covalently attached to lysine (Shuman, 1995). In yeast, mRNA capping enzyme consists of separate subunits for RNA 5'-triphosphatase and guanylyltransferase activities (Shibagaki, et al., 1992; Wang and Shatkin, 1984). cDNA clones coding for mRNA guanylyltransferase in *S. cerevisiae* (Shibagaki, et al., 1992), *S. pombe* (Shuman, et al., 1994), and *C. albicans* (Yamada-Okabe et al., 1996) have been sequenced. Each contains the active site lysine in KXDG (Fresco and Buratowski, 1994; Shuman, 1994), one of several highly conserved motifs characteristic of a superfamily of nucleotidyl transferases (Shuman and Schwer, 1995). A number of viral capping enzymes also contain these diagnostic sequence motifs, and the recently solved structure of capping enzyme from Chlorella virus PBCV-1 suggests that specific residues in these motifs are important for binding GTP (Hakansson, et al., 1997). Despite this detail of sequence and structure information, no metazoan capping enzyme has previously been cloned and characterized.

In order to gain a more complete understanding of the role of the cap in mammalian RNA metabolism, human ESTs homologous to the cloned *S. cerevisiae* RNA (guanine-7-) methyltransferase were identified and used to clone a cDNA encoding the human enzyme (hMet). hMet contains several motifs that are conserved among other RNA (guanine-7-) methyltransferases. In the presence of S-adenosylmethionine (Adomet), purified recombinant hMet converted the GpppG ends of transcripts to m$^7$GpppG. In addition, hMet formed ternary complexes with human capping enzyme (HCE) and the hyperphosphorylated elongating form of human RNA polymerase II (pol IIo).

The following examples are presented in order to more fully illustrate the preferred embodiments of the invention. They should in no way be construed, however, as limiting the broad scope of the invention. While the invention is described and illustrated herein by references to various specific material, procedures and examples, it is understood that the invention is not restricted to the particular material combinations of material, and procedures selected for that purpose. Numerous variations of such details can be implied as will be appreciated by those skilled in the art.

The present application contains nucleotide and protein sequence information in both a sequence listing and in the FIGURES. The sequence information in the FIGURES is believed to be identical to the corresponding sequence information appearing in the sequence listing. In the event of a discrepancy between the two, the recitation in the sequence listing should be considered as accurate and controlling.

EXAMPLES

Example 1

Mammalian Capping Enzyme Complements Mutant *Saccharomyces cerevisiae* Lacking mRNA Guanylyltransferase and Selectively Binds the Elongating Form of RNA Polymerase II.

Introduction

5'-Capping is an early mRNA modification that has important consequences for downstream events in gene expression. Mammalian cDNAs encoding capping enzyme have been isolated (Yue, et al., PNAS 1997). They contain the sequence motifs characteristic of the nucleotidyl transferase superfamily. The predicted mouse and human enzymes consist of 597 amino acids and are 95% identical. Mouse cDNA directed synthesis of a guanylylated 68-kDa polypeptide that also contained RNA 5'-triphosphatase activity and catalyzed formation of RNA 5'-terminal GpppG. A haploid strain of *Saccharomyces cerevisiae* lacking mRNA guanylyltransferase was complemented for growth by the mouse cDNA. Conversion of Lys-294 in the KXDG-conserved motif eliminated both guanylylation and complementation, identifying it as the active site. The K294A mutant retained RNA 5'-triphosphatase activity, which was eliminated by N-terminal truncation. Full-length capping enzyme and an active C-terminal fragment bound to the elongating form and not to the initiating form of polymerase. The results document functional conservation of eukaryotic mRNA guanylyltransferases from yeast to mammals and indicate that the phosphorylated C-terminal domain of RNA polymerase II couples capping to transcription elongation. These results also explain the selective capping of RNA polymerase II transcripts.

To explore the molecular interactions that result in selective capping of RNA polymerase II (pol II) transcripts in mammalian cells, cDNA clones that code for the human and mouse capping enzymes were isolated and characterized. Functional studies demonstrated that the mammalian enzyme complements the lethality of a *S. cerevisiae* mutant (CEG1[−]) lacking mRNA guanylyltransferase and binds selectively to the elongating form of RNA pol II in which the largest subunit contains a phosphorylated C-terminal domain (CTD).

Results

Nucleotidyl Transferase Superfamily Sequence Motifs Are Conserved in Human and Mouse mRNA Capping Enzymes. One human and two mouse cDNAs encoding mRNA guanylyltransferase were isolated. Each contains a single ORF of 1,794 bp that begins with the first ATG in an initiator consensus sequence (27) (FIG. 1A). The 3' untranslated region sequence of the shorter mouse clone is repeated in the longer one, which also has a second AATAAA polyadenylation signal. Complete sequences of the predicted polypeptides are shown in FIG. 1B. (See Seq.ID.No.: 1, GenBank Accession No.: AF025653 (MCE nucleotide), Seq.ID.No.: 4 (MCE amino acid), Seq.ID.No.: 2 GenBank Accession No.: AF025654 (HCE nucleotide) and Seq.ID.No.: 5 (HCE amino acid)). The mouse and human predicted proteins are 95% identical and consist of 597 amino acids with calculated molecular masses that are in close agreement with the 68 kDa reported previously for mammalian capping enzymes (10, 28). reported previously for mammalian capping enzymes (10, 28).

mRNA capping proceeds by removal of the [y]-phosphate from 5'-triphosphate termini followed by GMP transfer from guanylylated capping enzyme intermediate to the resulting 5'-diphosphate ends. In yeast, these reactions are catalyzed by an 80-kDa RNA 5'-triphosphatase and a 52-kDa mRNA guanylyltransferase, whereas in mammals both activities apparently are present as distinct domains of a single polypeptide (10). Sequence alignment of the C-terminal regions of the mammalian clones and *C. elegans* CEL-1 gene (19) with yeast guanylyltransferases indicates that they contain the conserved sequence motifs that identify members of the nucleotidyl transferase superfamily (16) (FIG. 2). These include a KXDG motif (bracket), which corresponds to the active site, guanylylated lysine in a variety of viral and cellular capping enzymes. viral and cellular capping enzymes.

Figure 3B:
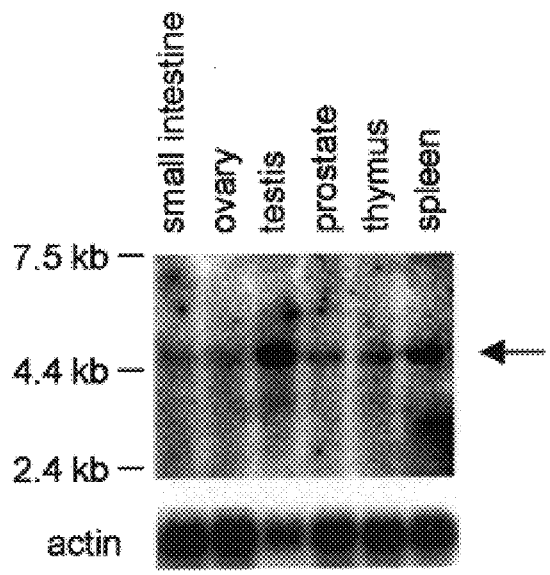

Capping Enzyme Expression In Vivo and In Vitro. Northern analysis of poly(A)+ RNA from mouse embryos and several adult tissues revealed two specific transcripts (FIG. 3A, arrows), consistent with the two mouse cDNA clones that differed in the sizes of the 3'-untranslated regions. Human tissues contained a single transcript (FIG. 3B). (FIG. 3B).

MCE cDNAs corresponding to the full-length wild type or a K294A mutant protein, or a C-terminal fragment beginning with amino acid 211 (Δ210), were inserted into a T7 expression vector and used in a coupled transcription/translation system. Products of the expected sizes were detected by [$^{35}$S]methionine labeling and SDS/PAGE (FIG. 4A). A cDNA encoding luciferase (Luc) served as a control. The MCEs, but not Luc, were immunoprecipitated with αMCE (FIG. 4B). immunoprecipitated with αMCE (FIG. 4B).

Figure 5A:
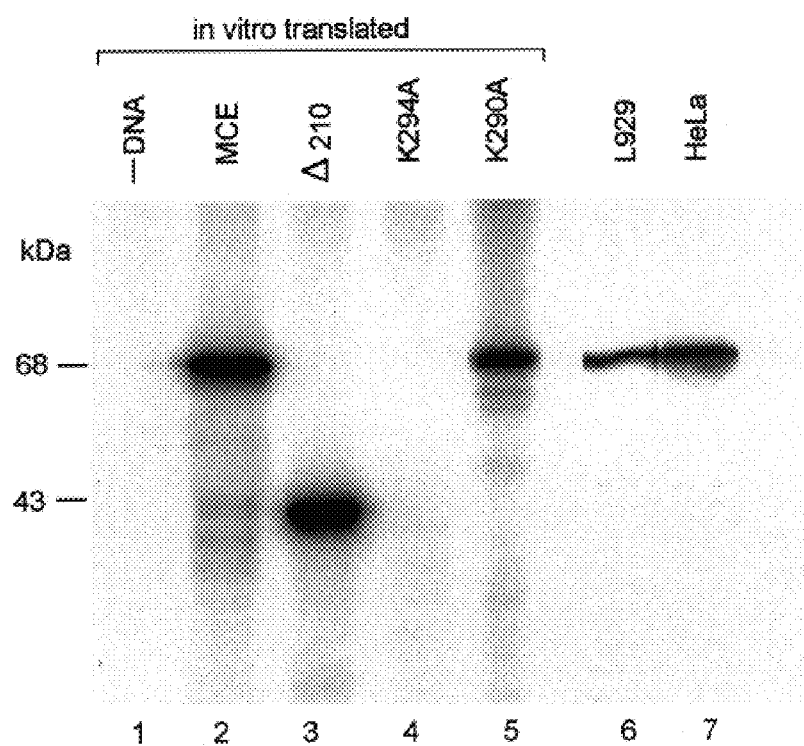
FIGS. 5A–5B. Guanylyltransferase activity of MCEs.

Guanylyltransferase Activity and Identification of the Active Site. To test for covalent attachment of GMP to the polypeptide encoded by the isolated mouse cDNA, proteins made in vitro were immunoprecipitated with αMCE, incubated with α[$^{32}$P]GTP and analyzed by SDS/PAGE. As shown in FIG. 5A, the full-length wild-type and K290A mutant proteins, as well as the C-terminal fragment, were guanylylated. Immunoprecipitates of samples from HeLa and mouse L cells also yielded a 32P-labeled polypeptide that comigrated with the full-length guanylylated in vitro products. To verify that Lys-294 in the KXDG motif is the site of guanylylation, the Lys was mutated to Ala. Although similar amounts of the K294A mutant and wild-type proteins were synthesized (FIG. 4A), the K294A mutant protein (unlike mutant K290A) was not guanylylated (FIG. 5A). (unlike mutant K290A) was not guanylylated (FIG. 5A).

Figure 5B:
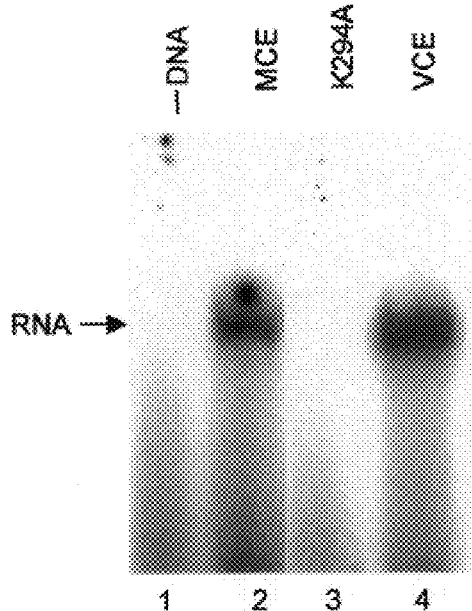
Figure 5C:
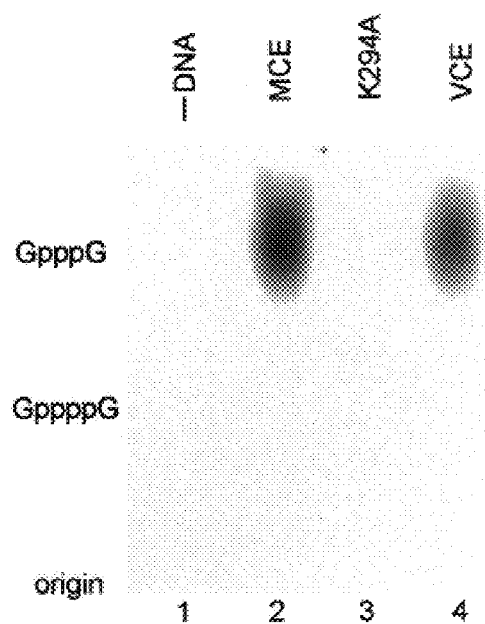

Capping enzymes synthesized in vitro were immunoprecipitated and tested for cap formation on T7 transcripts (presumably containing 5'-terminal pppG). The wild-type enzyme (FIG. 5B, lane 2), like purified vaccinia virus capping enzyme (FIG. 5B, lane 4), catalyzed transfer of radiolabeled GMP from α[$^{32}$P]GTP to the RNA, whereas the K294A mutant (lane 3) was inactive. 32P-labeled RNA samples were treated with P1 nuclease and phosphatase (CIAP) under conditions that convert capped RNAs to Pi and caps (29), and the digests were analyzed by TLC together with authentic GpppG and GppppG as markers. As shown in FIG. 5C, mouse and vaccinia virus capping enzymes both produced GpppG caps on the T7 transcripts. In the presence of S-adenosylmethionine, vaccinia, but not MCE, produced methylated caps. The results suggest that recombinant mammalian capping enzyme contains RNA 5'-triphosphatase in addition to guanylyltransferase activity.

Figure 6A:
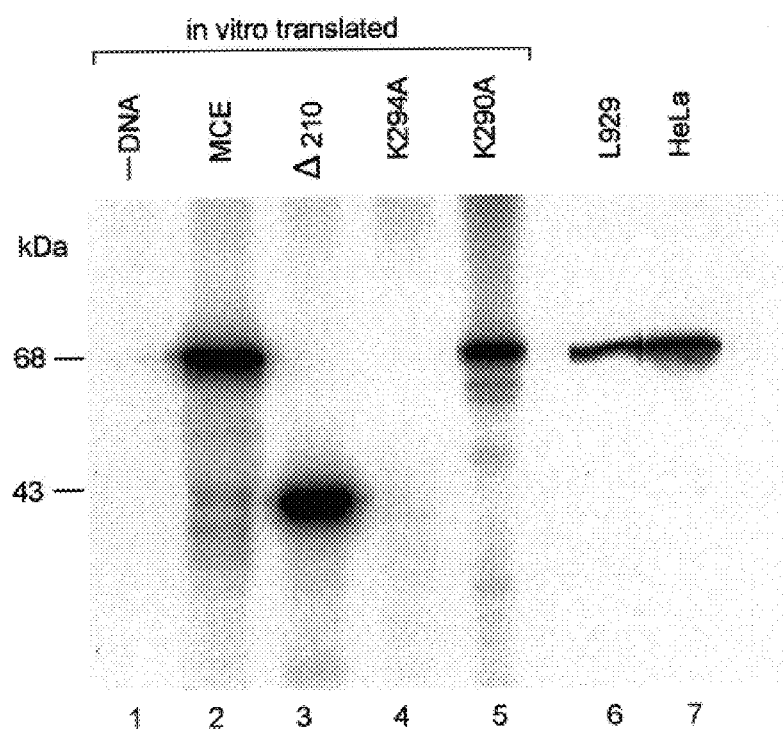
FIG. 6. MCE contains RNA 5'-triphosphatase. RNA containing 5'-terminal $\gamma[^{32}P]GTP$, prepared as described in Materials and Methods, was incubated with in vitro-synthesized, immunoprecipitated MCE wild type (lane 2), mutant K294A (lane 3), N-terminal truncation mutants Δ210 (lane 4), and Δ144 (lane 5) or vaccinia virus capping enzyme (lane 1). Samples were analyzed for release of labeled Pi by TLC and autoradiography.
Figure 6B:
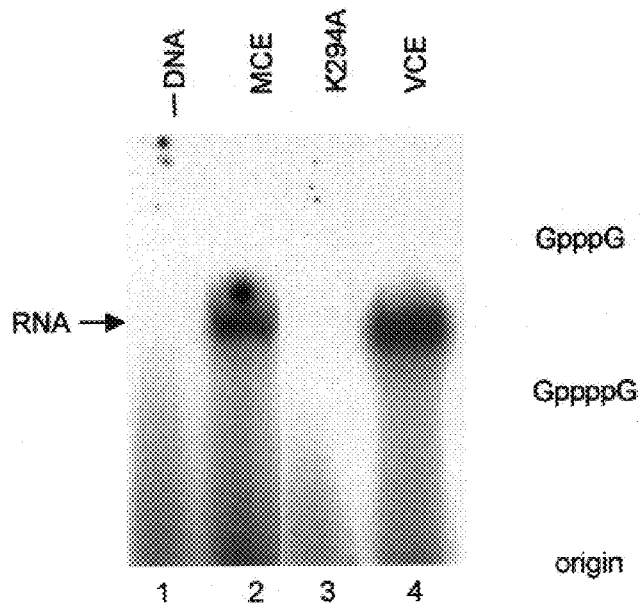
Figure 6C:
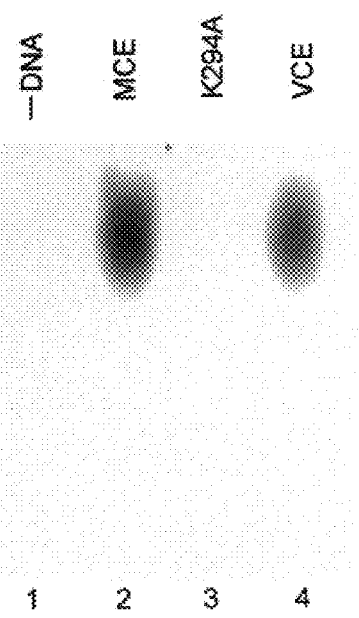

MCE Contains RNA 5'-Triphosphatase. Mouse and human capping enzymes and the related *C. elegans* CEL-1 ORF have N-terminal extensions that are absent from yeast mRNA guanylyltransferases and contain a stretch of 15 identical amino acids, GVHCTHGFNRTGFLI (Seq.ID.No.: 7). It includes (I/V)HCxxGxxR(S/T)G, a motif characteristic of protein tyrosine phosphatases (30, 31). However, CEL-1 encodes RNA 5'-triphosphatase rather than protein phosphatase activity (19). Treatment of γ[32P]GTP, 5'-end-labeled T7 transcripts with wild-type (FIG. 6, lane 2) or mutant K294A (FIG. 6, lane 3) MCE generated 32Pi, as did incubation with vaccinia capping enzyme (FIG. 6, lane 1). N-terminal truncation of 144 (FIG. 6, lane 5) or 210 (FIG. 6, lane 4) amino acids resulted in C-terminal fragments that were without RNA 5'-triphosphatase but retained guanylyltransferase (FIG. 5A, lane 3). Thus, the N-terminal region of mammalian capping enzyme is required for RNA 5'-triphosphatase but not for mRNA guanylyltransferase activity. guanylyltransferase activity.

Figure 7:
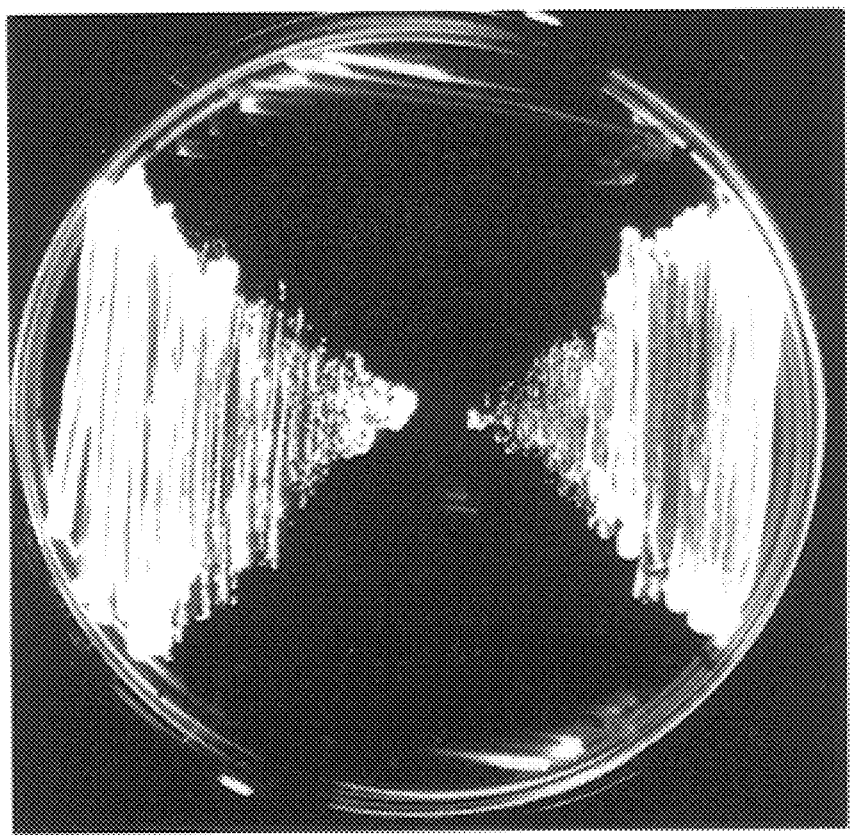
FIG. 7. Complementation of S. cerevisiae lacking mRNA guanylyltransferase. Growth was measured on selective media using CEG1[–] cells transformed with empty parental pG-1 (vector), pG-1 containing wild-type (MCE) or mutant (K294A) MCE or with a CEG1-containing URA3 plasmid (CEG1) as detailed in Materials and Methods.

Mammalian Capping Enzyme Complements *S. cerevisiae* ΔCEG1 Mutant. YBS2, a haploid *S. cerevisiae* strain in which the chromosomal CEG1 (mRNA guanylyltransferase) gene is deleted, is kept viable by the presence of an extrachromosomal allele supplied on a URA3 plasmid. A plasmid shuffle strategy (24) was used to determine if the mouse MCE gene can supply the essential mRNA guanylyltransferase function. Plasmids pG-MCE and pG-MCE (K294A) that constitutively express wild-type and mutant alleles of MCE and carry a TRP1 marker were introduced into YBS2 cells. Trp+ transformants then were plated on medium containing 5-fluoroorotic acid. As shown in FIG. 7, wild-type MCE sustained growth of YBS2 on counterselective medium, similar to control cells containing pGYCE358 (CEG1 and TRP1). By contrast, the K294A active site mutant that was devoid of mRNA guanylyltransferase activity did not complement YBS2 for growth on 5-fluoroorotic acid. Cells containing the empty parental vector pG-1 also failed to grow on 5-fluoroorotic acid. These results demonstrate that the mouse MCE gene fully complements *S. cerevisiae* ΔCEG1 mutant for growth. for growth.

Figure 8A:
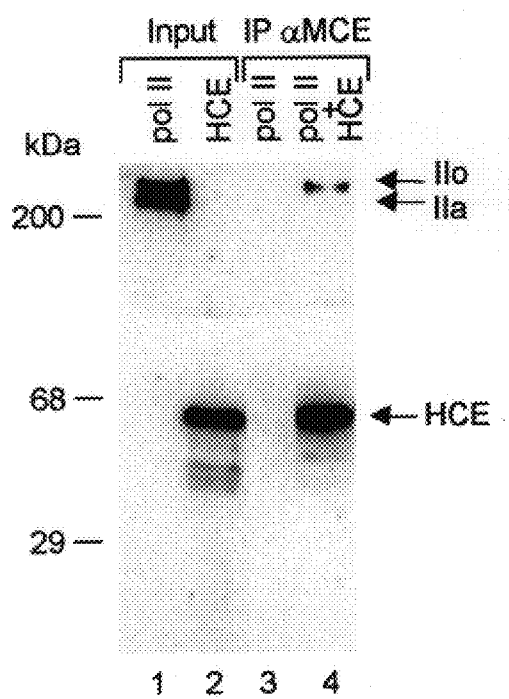
FIGS. 8A–8B. Capping enzyme directly interacts with the phosphorylated form of RNA pol II.

Selective Binding of Full-Length and C-Terminal Fragment of Mammalian Capping Enzyme to the Elongating Form of pol II. Because addition of the cap to mRNA occurs early during transcription (32–34), it was important to investigate whether capping enzyme is part of the human pol II holoenzyme (35). Surprisingly, it was found that it is not. Therefore it was tested for the direct interaction of capping enzyme with pol II. Immunocomplexes containing human capping enzyme were incubated with purified human RNA pol II that contains approximately equal amounts of the initiating (nonphosphorylated CTD) and elongating (phosphorylated CTD) forms of the enzyme (FIG. 8A, lane 1). Western blot analysis demonstrated that αMCE specifically immunoprecipitated the elongating form of pol II (FIG. 8A, lane 4). Selective immunoprecipitation of the phosphorylated form of pol II was not because of a nonspecific interaction of the antibodies as it was dependent on the presence of capping enzyme (FIG. 8A, lane 3). it was dependent on the presence of capping enzyme (FIG. 8A, lane 3).

Figure 8B:
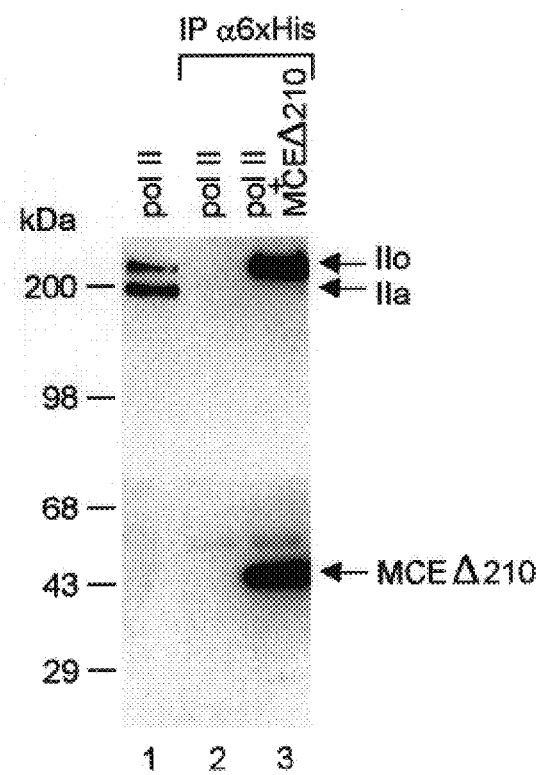

The C-terminal guanylyltransferase domain of capping enzyme was sufficient for interaction with pol II. Consistent with the results in FIG. 8A, the phosphorylated form of pol II was specifically coimmunoprecipitated with 6×His-tagged MCE Δ210 in the presence of anti-hexahistidine antibody (FIG. 8B, lane 3), and this was dependent on the presence of capping enzyme (FIG. 8B, lane 2). It was concluded that the C-terminal guanylyltransferase domain of capping enzyme directly interacts with the elongation competent, phosphorylated form of RNA pol II.

Discussion

The functional importance of mRNA 5'-capping in the control of eukaryotic gene expression has been demonstrated at several levels, including pre-mRNA synthesis and splicing in the nucleus, mRNA transport to the cytoplasm, ribosome binding during translation initiation, and transcript turnover. The presence of a 5'-terminal cap impacts on each of these stages in the lifetime of cellular mRNAs, and mRNA capping is essential for viability in *S. cerevisiae*. In addition, most viruses that replicate in the cytoplasm have evolved mechanisms to assure that the viral mRNAs are capped.

In mammalian cells, caps are added exclusively to newly initiated RNA pol II transcripts. Presumably, this specificity is based on the selective association of capping enzyme with one or more subunits of pol II. The results presented in FIG. 8 directly demonstrate an interaction between capping enzyme and pol II and suggest that CTD phosphorylation regulates this interaction. Previous studies have demonstrated that CTD phosphorylation regulates pol II function during the transcription cycle, most likely by selecting interacting factors (36, 37). The form of pol II that associates with transcription initiation complexes contains an unphosphorylated CTD, whereas the pol II engaged in elongation contains a phosphorylated CTD (36). The unphosphorylated form of pol II selectively interacts with the TATA-binding protein (38), TFIIE (39), and presumably other general transcription initiation factors (40), as well as with a large number of other initiation factors that regulate transcription efficiency and are components of a large polymerase complex, the so-called pol II holoenzyme (35, 41–43).

Recent studies have shown that pol II also interacts with factors involved in RNA processing (44, 45), and it has been hypothesized that these interactions are established after CTD phosphorylation (44, 46). Our results demonstrating a specific interaction between capping enzyme and the phosphorylated form of pol II further support this hypothesis. The studies of Hagler and Shuman (34), using the vaccinia virus transcription system, demonstrated that the cap structure is added immediately after the 5'-end of the nascent RNA is exposed (after formation of 30 phosphodiester bonds). Lis and coworkers (33), using the Drosophila HSP70 gene, arrived at a similar conclusion. In intact isolated nuclei, the uninduced HSP70 gene contains an RNA pol II engaged in transcription but paused approximately 25–30 nucleotides downstream of the transcription start site. The CTD of the paused RNA pol II is unphosphorylated. Early after heat shock induction, the pol II enters into a productive elongation mode that is accompanied by phosphorylation of the CTD (47). Analysis of the formation of the cap at the Drosophila heat shock locus established that the paused RNAs are mostly uncapped, but become capped after the formation of approximately 30 phosphodiester bonds (33). Based on our results establishing that capping enzyme interacts preferentially with pol II containing a phosphorylated CTD, it was proposed that concomitant to entry into the elongation mode, pol II interacts with capping enzyme and the nascent RNA becomes capped. This event, together with CTD phosphorylation, results in a signal for the association of the RNA processing machinery with the transcribing (elongating) machinery. In this model, 3' extension of 5'-uncapped and exonuclease-sensitive transcripts is avoided, possibly another example of CTD-mediated mRNA quality assurance (48, 49).

It is perhaps noteworthy in light of capping enzyme binding to the elongating form of pol II that the presence of a 5'-cap is a prerequisite for 3'-processing of histone mRNA (50) and possibly other transcripts (51). In addition, termination of influenza virus mRNA synthesis is cap-dependent (52), and vaccinia virus mRNA termination requires the presence of viral capping enzyme (53). Recent studies indicate that the human capping enzyme gene is on chromosome 6, and further analysis may uncover linkages between this key enzyme and hereditary disorders as recently described for transcription factors (54, 55).

Materials and Methods

Cloning of Mouse and Human Capping Enzyme cDNAs. To identify genes encoding mammalian mRNA capping enzymes, the BLAST server at the National Center for Biotechnology Information (18) was used to screen the nonredundant GenBank Database Expressed Sequence Tag (EST) Division by querying with the amino acid sequence of *S. pombe* mRNA guanylyltransferase, PCE1 (accession no. U16143) (13). Two mouse expressed sequence tags (EST accession nos. AA096583 and AA108985) that displayed significant identity to the C-terminal half of PCE1 were identified and overlapped to predict a partial ORF with homology to PCE1 C-terminal sequence. A BLAST search of the nonredundant GenBank coding sequences using the mouse partial ORF demonstrated its homology to PCE1 as well as to *Caenorhabditis elegans* CEL-1 (19) and *S. cerevisiae* CEG1 (m-RNA guanylyltransferase) (9) gene product.

Mouse capping enzyme (MCE) cDNAs were cloned from embryo poly(A)+ RNA (Ambion) by Marathon cDNA amplification according to the manufacturer's instructions (CLONTECH). Gene-specific primers GSP1 (5'-GGGCGGCTGCTGCACATCTGTCAATG-3') (Seq.ID.No.: 8) and GSP2 (5'-CCCAAATGCCTACAACACAGCCATGGC-3') (Seq.ID.No.: 9) based on the EST sequences were used for 5'- and 3'-rapid amplification of cDNA ends (RACE) reactions. The resulting single 5'-RACE fragment (1.8 kb) and two 3'-RACE fragments (0.8 kb and 2.3 kb) were cloned into pCR2.1 (Invitrogen) and sequenced by using an Applied Biosystems-373 automated sequencer. The EST also was used to screen a HeLa cDNA library (Stratagene), and a 4.5-kb cDNA insert recovered in pBluescript SK was sequenced as above.

Northern Blot Analysis. EST AA096583 and human β-actin cDNA (CLONTECH) were used to probe mouse and human multiple tissue and mouse embryo Northern blots as recommended by the manufacturer (CLONTECH).

Plasmids. All MCE constructs generated by PCR (Advantage KlenTaq polymerase, CLONTECH) or site-specific mutagenesis (QuikChange Kit, Stratagene) first were cloned into pCR2.1 with a BamHI site at the 5' end. N-terminal truncation mutant Δ210 was further subcloned into the BamHI site of pET-28a (Novagen). A 5'XhoI-3'KpnI fragment coding for wild-type or K294A mutant MCE was isolated from pCR2.1, blunted with Klenow and ligated to SalI-digested, Klenow-treated pG-1 (20) to yield pG-MCE.

Expression of MCE Fragment and Antibody Production. Based on the combined nucleotide sequence of the mouse ESTs, a DNA fragment encoding a C-terminal region (amino acids 438–597) of the MCE with a 6xHis tag was obtained by PCR by using as template mouse embryo cDNA (Marathon ready, CLONTECH). The purified PCR product was cloned into pCR2.1, and the insert then was excised with NheI and BamHI and cloned in-frame in pET-11a (Novagen) to generate pMCE0.5. Recombinant protein expressed in *Escherichia coli* BL21 (DE3) transformed with pMCE0.5 was purified on Ni-nitrilotriacetic acid agarose (Qiagen) and used to raise antibodies (αMCE) in rabbits.

In Vitro Translation and Immunoprecipitation. pCR2.1 plasmids containing wild-type or mutant MCE were used to synthesize proteins in the TNT Coupled Reticulate Lysate System (Promega). Products were immunoprecipitated with αMCE in 25 mM Tris, pH 7.5/100 mM KCl/5 mM MgCl/0.5 mM DTT (buffer B).

MCE Guanylylation and RNA Cap Formation. Vaccinia virus capping enzyme (1 unit, GIBCO/BRL) or translated and immunoprecipitated proteins prepared as above from 50

µl TNT lysate were incubated for 15 min at 37° C. in 20 µl of GTP-labeling buffer consisting of 25 mM Tris at pH 7.5, 5 mM MgCl2, 0.5 mM DTT, α[$^{32}$P]GTP (10 µCi, 3,000 Ci/mmol, Amersham), and 0.10 µg inorganic pyrophosphatase (Boehringer). Guanylylation of proteins was analyzed by SDS/PAGE followed by autoradiography. T7 polymerase run-off RNA (32-mer) transcribed from BamHI-linearized pGEM1 (Promega) was incubated as indicated in GTP-labeling buffer for 15 min at 37° C. Samples were extracted with phenol/chloroform, precipitated with ethanol, and analyzed by 8% PAGE. For analysis of cap formation, RNA after extraction was passed through a Chroma Spin-10 column (CLONTECH), precipitated with ethanol, resuspended in 8 µl of 50 mM sodium acetate (pH 5.3) containing 4 µg P1 nuclease (Boehringer) and incubated at 37° C. for 1 hr. Samples were adjusted to 50 mM Tris (pH 8.0), treated with calf intestine alkaline phosphatase (1 unit, GIBCO/BRL) for 30 min at 37° C. (21), spotted on polyethyleneimine-cellulose plates, and analyzed by TLC in 0.4 M ammonium sulfate followed by autoradiography.

RNA 5'-Triphosphatase Assay. RNA (32-mer) was synthesized as above except that GTP was replaced with γ[$^{32}$P]GTP (30 µCi, 30 Ci/mmol, DuPont). The 5' end-labeled RNA was purified by passage through a Chroma Spin-10 column and incubated for 15 min at 37° C. with the indicated proteins in GTP-labeling buffer but without α[$^{32}$P]GTP and inorganic pyrophosphatase (4×10$^4$ cpm, 15 µl). Reaction products were extracted with phenol/chloroform and analyzed by polyethyleneimine-cellulose TLC in 0.8 M acetic acid containing 0.9 M LiCl followed by autoradiography.

Complementation of a Yeast mRNA Guanylyltransferase Mutant by MCE. pG-1 (CEN and TRP1; ref 20) was used to express MCE under control of the constitutive yeast glyceraldehyde-3-phosphate dehydrogenase promoter. The haploid S. cerevisiae strain YBS2 [MATa, leu2, lys2, trp1, ceg1::hisG, pGYCE-360 (CEN, URA3, CEG1)] (22) was transformed with either wild-type or mutant pG-MCE by using the lithium acetate method (23). Trp+ transformants obtained at 30° C. were tested for the ability to grow in the presence of 5-fluoroorotic acid, which selects against cells that retain the CEG1-containing URA3 plasmid (24).

Pol II-Capping Enzyme Interaction Studies. αMCE (1 µg), affinity purified using MCE Δ210 bound to Affi-prep 10 (Bio-Rad) Resin, was incubated with protein A-agarose (Repligen) beads for 30 min at room temperature. The antibody-protein A beads were washed and equilibrated with Hepes buffer, pH 7.8 containing 0.1 M KCl and 0.1% Nonidet P-40 (buffer I) and then incubated with or without partially purified (25) HeLa capping enzyme (120 µg) for 1 hr, rotating at 4° C. This immune complex was washed extensively with buffer I containing 1M KCl and equilibrated with buffer I before incubation for 1 hr, rotating at 4° C. with pol II (1.2 µg of DEAE-5PW protein fraction; ref 26). The immune complexes again were washed extensively, equilibrated with buffer I, and used for Western blot analysis. Blots were developed with αMCE and antibodies against the pol II largest subunit by ECL (Boehringer Mannheim).

Immunoprecipitation of 6×His-tagged MCE Δ210 was performed using mAbs against hexa-histidine tag (CLONTECH). One microgram of antibodies was incubated with protein G-agarose beads (Boehringer Mannheim) for 30 min at room temperature, and the resulting complexes were washed and equilibrated with buffer I, incubated with purified MCE Δ210 (0.25 µg), and processed as above.

Example 2
Recombinant Human mRNA Cap Methyltransferase Binds Capping Enzyme/RNA Polymerase IIo Complexes Introduction
Guanine N-7-methylation is an essential step in the formation of the m$^7$GpppN cap structure that is characteristic of eukaryotic mRNA 5' ends. The terminal 7-methylguanosine is recognized by cap binding proteins that facilitate key events in gene expression including mRNA processing, transport and translation. Herein the cloning, primary structure and properties of human RNA (guanine-7-) methyltransferase is disclosed. Sequence alignment of the 476-amino acid human protein with the corresponding yeast ABD1 enzyme demonstrated the presence of several conserved motifs known to be required for methyltransferase activity. A Drosophila ORF that encodes a putative RNA (guanine-7-) methyltransferase and contains these motifs has now been identified and is disclosed herein. Recombinant human methyltransferase transferred a methyl group from S-adenosylmethionine to GpppG 5'ends which are formed on RNA polymerase II transcripts by the sequential action of RNA 5'-triphosphatase and guanylyltransferase activities in the bifunctional mammalian capping enzyme. Binding studies demonstrated that the human cap methyltransferase associated with recombinant capping enzyme. Consistent with selective capping of RNA polymerase II transcripts, methyltransferase also formed ternary complexes with capping enzyme and the elongating form of RNA polymerase II.

Results
Cloning and expression of a cDNA encoding human RNA (guanine-7-) methyltransferase. A human cDNA containing a single ORF of 1431 bp encoding hMet was isolated based on sequence homology to the S. cerevisiae, C. elegans, and Drosophila enzymes. The predicted protein consists of 476 amino acids (Seq.ID.No.: 6) with a calculated molecular weight of ~55 kDa which is in close agreement with that reported earlier for the purified enzyme (85). hMet shows significant homology to its counterparts from yeast (82) and C. elegans (C25A1.f gene product, 86). Genbank searches also revealed an ORF from Drosophila that encodes a putative RNA (guanine-7-) methyltransferase. Alignment of the predicted amino acid sequence of the human enzyme with the yeast, C. elegans and Drosophila proteins indicates the presence of several conserved motifs (FIG. 9). Three motifs have been described as characteristic of diverse methyltransferases including motif I, VL(D/E)XGXGXG, which has been shown to be part of the AdoMet binding pocket (87, 88). hMet contains this conserved motif (residues 201–209) and the previously described motif III (residues 308–316) but not motif II (FIG. 9). This is expected since motif II is known to be absent in RNA methyltransferases (87). hMet also shows homology to methyltransferases from vaccinia virus and Shope fibroma virus within these motifs. In addition, a conserved sequence was identified near the C-terminus, GTLSKSEWEA (Seq.ID.No.: 10) (referred to as motif X), that is completely conserved in human, (C. elegans, and Drosophila but absent in yeast ABD1 (FIG. 9).

Figure 10:
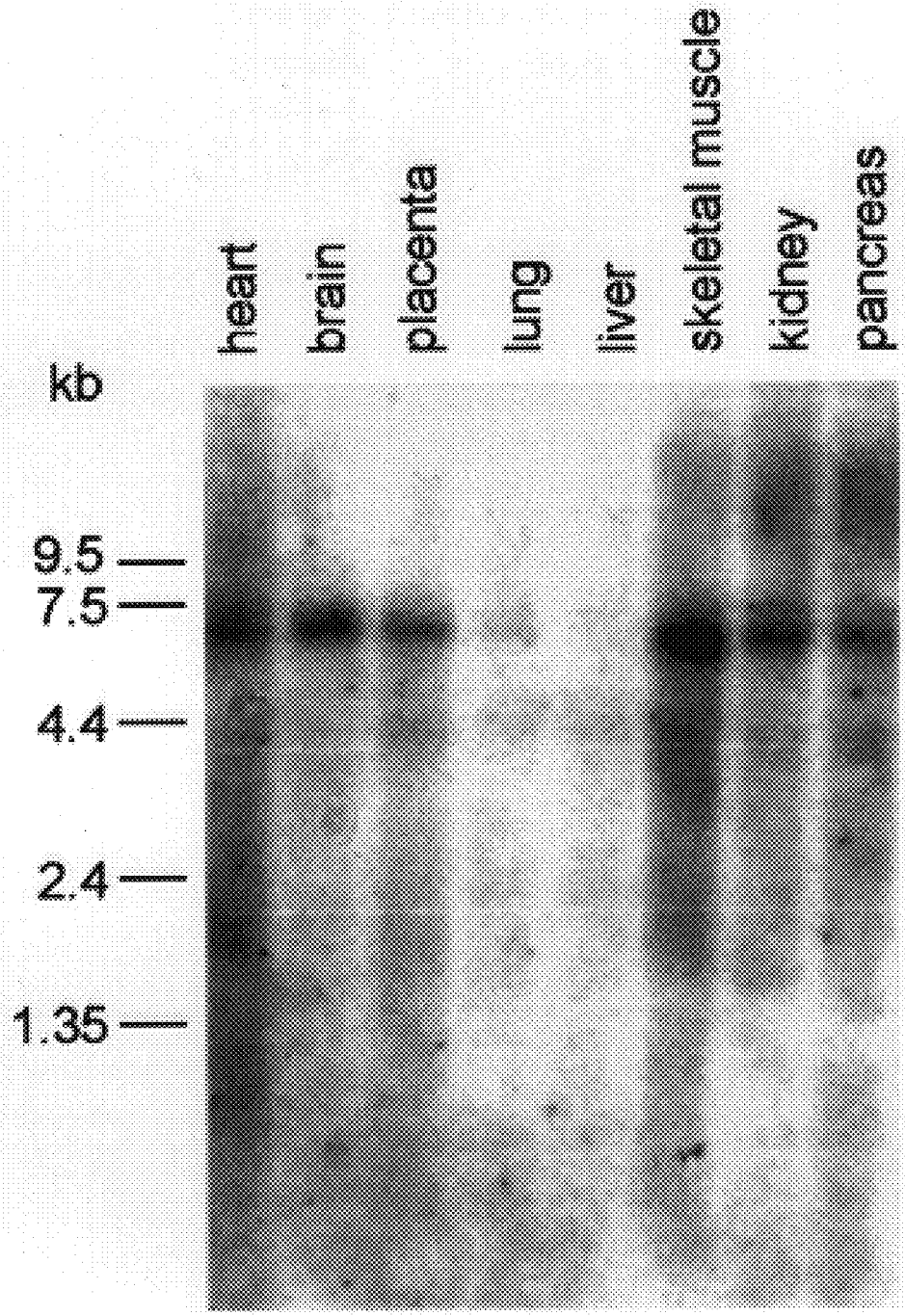
FIG. 10. Northern blot analysis of hMet expression. Poly (A)+ RNAs from human adult tissues were probed with a 734 bp PCR fragment as described in Example 2, Materials and Methods.

Full length hMet cDNA is 6203 bp (Seq.ID.No.: 3, GenBank Accession No.: AF067791) and contains a single ORF of 1431 bp that starts with the initiator codon in the context TAAATGG. The 5'-untranslated region consists of 196 bp, while the 3'-untranslated region is strikingly longer, 4576 bp, and contains a polyadenylation signal, AATAAA 18 residues from the 3' end. Consistent with the length of the cloned hMet cDNA, northern blot analysis of poly (A)$^+$ RNA from normal adult human tissues revealed a specific transcript of 6.2 kb (FIG. 10).

Figure 11A:
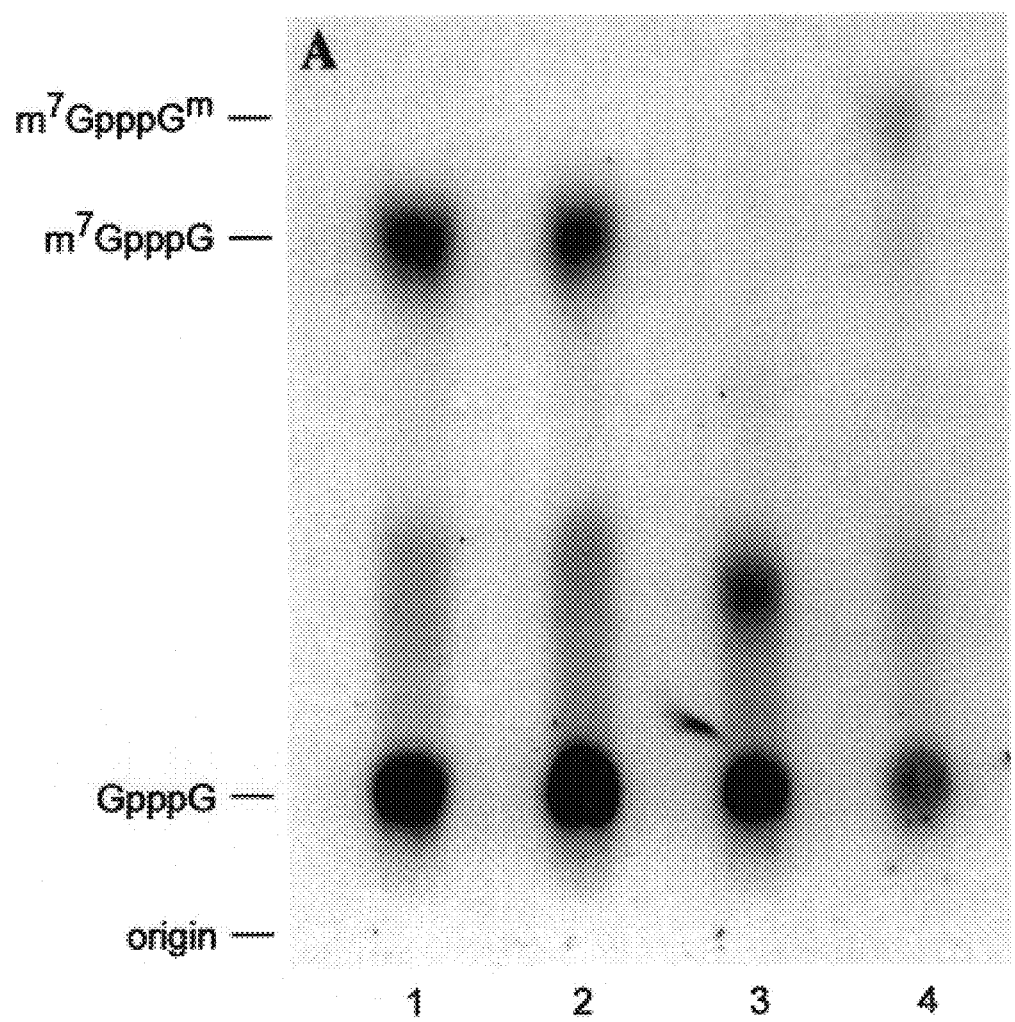

RNA (guanine-7-) methyltransferase activity of recombinant hMet. Purified GST-tagged hMet, either on glutathione beads or in solution, was incubated with Adomet and T7 run-off transcripts containing G$^{32}$pppG 5'ends. Samples were then digested with P1 nuclease and analyzed for methylation. As shown in FIG. 11A (lanes 1 and 2), recombinant hMet converted GpppG ends to m$^7$GpppG, while purified GST control (lane 3) did not show any methyltransferase activity. In contrast to hMet, vaccinia virus CE complex which contains both RNA (guanine-7-)methyl- and 2'(-O-methyl)-transferase activities (12) formed m$^7$GpppG$^m$ caps (lane 4). 6×His-tagged hMet 1–389 and full length proteins were also expressed in vitro, immobilized on protein A beads and assayed for RNA (guanine-7-) methyltransferase activity. Results of this experiment demonstrated that truncation of the C-terminal 87 amino acids eliminated methyltransferase activity (FIG. 11B).

Figure 12:
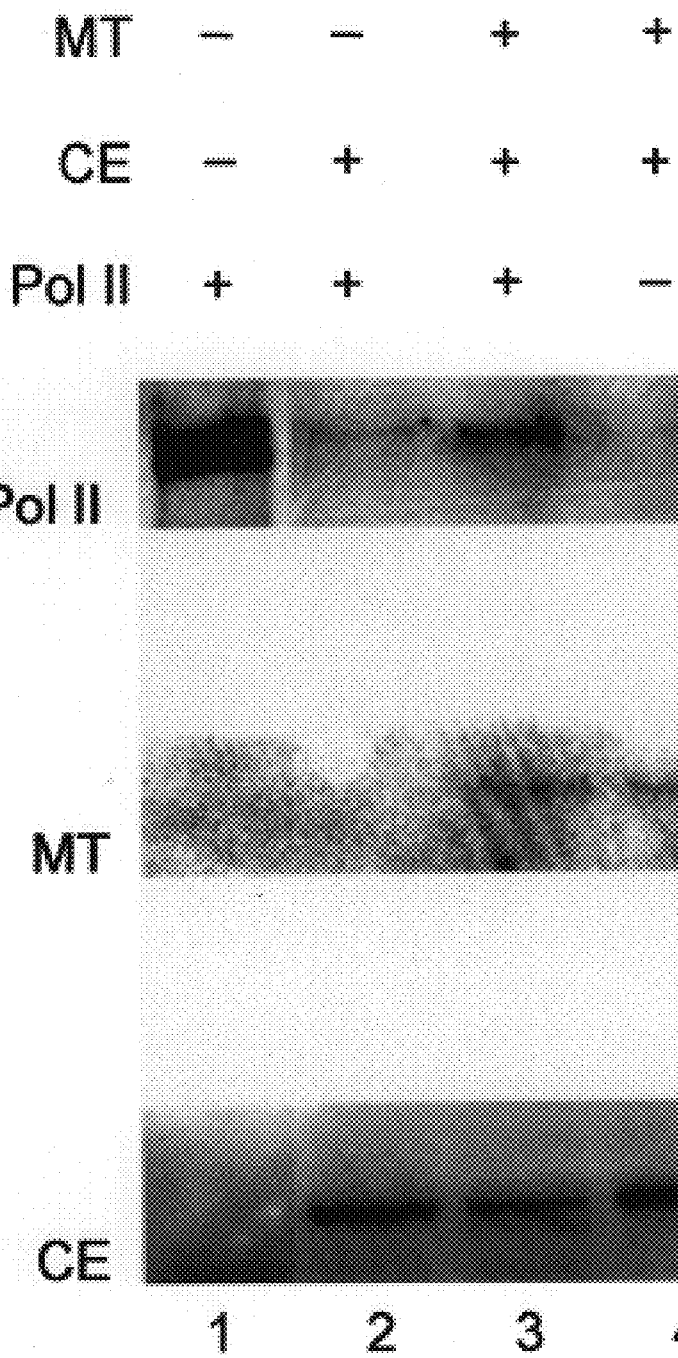
FIG. 12. Ternary complex formation of hMet with HCE and the elongating form of RNA pol II in vitro. Recombinant HCE bound to antibody-protein G beads was mixed with HeLa RNA pol II (lane 2), recombinant hMet and pol II (lane 3), or hMet alone (lane 4). Immunoprecipitates were washed extensively and analyzed by 4–20% gradient SDS-PAGE together with the input pol II containing approximately equal amounts of hyperphosphorylated pol IIo and unphosphorylated pol IIa (lane 1). Western blot analysis was done with antibodies against HCE (lower panel), hMet (middle panel) or the CTD of the largest subunit of pol II (upper panel).

Interactions of hMet with CE and the elongating form of RNA pol II in vitro. It has been shown that mammalian CE binds the hyperphosphorylated, elongating form of RNA polymerase II (62). Yeast methyltransferase has also been shown to bind selectively to the hyperphosphorylated CTD of yeast RNA pol II (53). It was therefore important to investigate whether hMet binds human RNA pol II. Immune complexes containing recombinant hMet on protein G beads did not form stable complexes with either the initiating (pol IIa) or elongating (pol IIo) form of RNA pol II but did bind recombinant HCE. On the basis of these results, formation of ternary complexes was tested for hMet, HCE and RNA pol II. Immune complexes containing HCE on protein G beads were incubated with purified human RNA pol II and/or hMet. Western blot analysis demonstrated that the elongating form of pol II was selectively immunoprecipitated with HCE (FIG. 12, lane 2) from a mixture containing approximately equal amounts of pol IIa and pol IIo (lane 1). HCE also bound hMet (FIG. 12, lane 4). When RNA pol II and hMet were incubated together with HCE, ternary complexes were formed (FIG. 12, lane 3). These results suggest that hMet may not interact with pol IIo by itself but forms complexes with HCE which binds to pol IIo. In this context it is of interest that the level of pol IIo immunoprecipitated by HCE increased in the presence of hMet (FIG. 12, compare lanes 2 and 3).

Discussion

The cap structure that is characteristic of RNA pol II transcripts consists of m$^7$G linked via a 5'-5' triphosphate bridge to the first residue in pre-mRNAs. Capping of nascent transcripts proceeds by the sequential action of RNA 5' triphosphatase, guanylyltransferase and guanine-7-methyltransferase to form the monomethylated cap 0 structure, m$^7$GpppN. Although typical of yeast mRNAs (89), cap 0 structures in higher eukaryotes are usually converted in the nucleus to m$^7$GpppN$^m$ cap 1 structures by 2'-O-methylation (56). Additional methylation can occur in the cytoplasm to form m$^7$GpppN$^m$pN$^m$ cap 2 structures (90–92). While the possible role(s) of cap 2'-O-ribose methylation are only beginning to be elucidated (93, 94), numerous important biological consequences have been described for m$^7$G.

Many if not all aspects of mRNA synthesis and function depend on cap-binding protein complexes that specifically recognize m$^7$GpppN. Ribosome binding during initiation of translation is facilitated by interactions of eIF4F with cap (66, 67). Nuclear events such as in pre-mRNA splicing, 3' end formation and nucleocytoplasmic transport are mediated by a different cap-binding protein complex (74). In addition, guanine N7-methylation of 5' ends can influence transcript stability both positively and negatively. Guanine N7-methylation blocks pyrophosphorolysis of GpppN structures which protect transcripts against 5' exonucleolytic degradation (68). On the other hand, the 7-methyl group contributes to the substrate specificity of the yeast mRNA decapping enzyme, Dcp1p (78) which increases transcript susceptibility to exonuclease.

Cap methylation studies have focused on virion-associated enzymes (66, 67) and on the yeast methyltransferase (82). Although cap methyltransferases have been purified from mammalian sources (85, 95) the corresponding gene was not previously cloned and characterized. The identification and primary structure of a human cDNA that encodes a protein with activity and sequence motifs characteristic of RNA methyltransferases (87, 88) is reported herein. A C-terminal truncation mutant of hMet (1–389) that retained previously identified methyltransferase motifs but not motif X was without enzymatic activity. However, motif X is not present in ABD1, and thus its possible role in RNA methylation needs to be further investigated. In this context, it is interesting to note that C-terminal deletion of as few as 55 amino acids from the 436-amino acid ABD1 protein was shown to be lethal (82). Comparison of the human and yeast sequences in this region shows several conserved residues (FIG. 9), but which if any are specifically required for methyl group transfer from Adomet to caps remains to be determined.

Selective capping of RNAs transcribed by pol II, but not pol I and III, was recently explained by the finding of specific association between capping enzymes and the hyperphosphorylated CTD of RNA polymerase II (62–64). Yeast RNA (guanine-7-) methyltransferase has also been shown by affinity chromatography to bind specifically to hyperphosphorylated GST-CTD (63). Although binding of full length hMet to pol II in immunoprecipitation experiments was not detected, preliminary studies of hMet 1–389 indicate that the truncation mutant can bind pol IIo. Thus association of hMet with pol II may be hindered by C-terminal residues (including motif X) that are not present in ABD1. Binding of hMet to HCE and to HCE/pol IIo complexes suggests that it is recruited to the transcription machinery by association with HCE.

Materials and Methods

Cloning of human RNA (guanine-7-) methyltransferase (hMet) cDNA. Yeast RNA (guanine-7-) methyltransferase (ABD1, acc. no. P32783) was used to search for homologous sequences in the expressed sequence tag (EST) division of Genbank using the BLAST server at the National Center for Biotechnology Information (83). Two human ESTs were identified (acc. nos. C04619 and C03306) that overlapped and displayed significant homology to ABD1. Searches with these ESTs yielded three additional, overlapping ESTs (acc. nos. AA566003, AA568320 and AA642424) that were assembled to predict a partial ORF coding for 389 amino acids of hMet. BLAST searches also identified an ORF from Drosophila (acc. no. AC002502) that encodes a putative RNA (guanine-7-) methyltransferase with homology to other methyltransferases.

The human EST sequences facilitated design of a gene-specific primer, met-GSP1: 5'-CTGCAGATGTCAAAACACATTTGTGGGTCACG-3' (Seq.ID.No.: 11) which was used to obtain the 5' untranslated region of hMet by rapid amplification of cDNA ends (RACE) with Marathon ready HeLa cDNA as template (CLONTECH). The resulting 1.2 kb 5'-RACE product was cloned into pCR2.1 (Invitrogen) and sequenced using an Applied Biosystems-373 automated sequencer. Several different primers designed from the EST sequences failed to amplify the complete 3' end of the hMet cDNA, possibly due to the presence of an internal A-rich stretch at codons 391–394. However, the 3' end of hMet was obtained by identifying a motif, GTLSKSEWEA (Seq.ID.No.: 12), near the C-terminus that was completely conserved between Drosophila and *C. elegans* (acc. no. Z81038). From the codon frequency usage within the hMet gene, primer met-DEG1: 5'-GCTTCCCATTCAGATTTAGAAAGAGTTCC-3' (Seq.ID.No.: 13) was designed for use in RACE to amplify the 3' end of the cDNA[1].

Northern blot analysis. A 734 bp fragment was obtained by PCR with HeLa cDNA as template and primers met-GSP1 and met-GSP2: 5'-GCTTCTGGGACTGGGCTTTGTGAAAAGAC-3' (Seq.ID.No.: 14). This fragment was used to probe human multiple tissue northern blots (CLONTECH) in ExpressHyb solution (CLONTECH) as recommended by the manufacturer.

Expression and purification of recombinant hMet and capping enzyme. A 390 bp DNA fragment encoding hMet 175–302 was amplified with the human EST (acc. no. C03306) as template and primers met-A1: 5'-GGATCCCCTAAGAACTTTAATAATTGGATGAAA-3' (Seq.ID.No.: 15) and met-A2: 5'-GGATTCGTTTCTCAGCATCATGTCAGCCTGCT-3' (Seq.ID.No.: 16). The resulting PCR product was digested with BamHI and EcoRI and cloned in-frame into pGEX-2T (Pharmacia). Recombinant, GST-tagged hMet 175–302 was expressed and purified from *E. coli* DH5a and used to raise antibodies (a-hMet) in rabbits.

DNA fragments encoding full length (amino acids 1–476) or C-terminally truncated (1–389) hMet were obtained by PCR with Hela cDNA template and primers met-P1: 5'-GCGGATCCATGGCAAATTCTGCAAAAGCAG-3' (Seq.ID.No.: 17) and met-P2: 5'-CGCTCGAGTCACTGCTGTTTCTCAAAGGC-3' (Seq.ID.No.: 18) for full length and met-P1 and met-P3: 5'-CGCTCGAGTCATAGTTTCATATTGTACTTC-3' (Seq.ID.No.: 19) for the 1–389 truncation. PCR products were cloned into pCR2.1. The BamHI-XhoI fragment encompassing the complete coding sequence was subcloned into pGEX-4T3 (Pharmacia) and expressed as a GST-fusion protein in *E. coli* BL21 (DE3) by induction with 10 mm IPTG for 9 hr at 30° C. Proteins were purified from bacterial lysates using standard protocols. Full length hMet and the 1–389 truncation, subcloned in pET28a (Novagen), were expressed in vitro as 6xHis-tagged proteins using the TNT Coupled Reticulocyte Lysate System (Promega).

Full length HCE cloned into a baculovirus expression vector, pBlueBacHis2A (Invitrogen), under the control of the polyhedrin promoter was introduced into Sf9 insect cells by transfection with the Bac-N-Blue transfection kit (Invitrogen). Recombinant virus was used to produce 6xHis-tagged HCE in Sf9 cells according to the manufacturer's instructions.

RNA (guanine-7-) methyltransferase activity assay. T7 polymerase run-off transcripts were synthesized and capped by incubation with vaccinia virus CE in the presence of a-$^{32}$P-GTP (7). Purified transcripts containing $^{32}$P-labeled GpppG 5'ends were incubated in 20 ml reaction mixtures containing 50 mM Tris pH 8.0, 2mM DTT, 50 mM Adomet and recombinant GST-hMet (2.5 mg) at 37° C. for 30 min. After phenol/chloroform extraction and ethanol precipitation, the RNA samples were dissolved in 10 ml of 50 mM sodium acetate, pH 5.3 and digested with 4 mg of P1 nuclease at 37° C. for 30 min. Digests were spotted on PEI-TLC plates, resolved in 0.4M ammonium sulfate and analyzed by autoradiography (62). GpppG, m$^7$GpppG and m$^7$GpppG$^m$ standards resolved alongside were detected under UV illumination.

Interaction of hMet with pol II and HCE. a-His (mAb against 6xHis, 1 mg, CLONTECH) was incubated with protein G-agarose beads (Boehringer Mannheim) for 30 min at room temperature. The antibody-protein G beads were washed and equilibrated with buffer A (50 mM Tris pH 7.85, 100 mM KCl, 0.1% Nonidet P-40) and then incubated with purified, recombinant 6xHis-tagged HCE (0.25 mg) for 1 hr at 4° C. The immune complexes were washed extensively with buffer A and incubated for 1 hr at 4° C. with pol II (1.2 mg of DEAE-5PW HeLa protein fraction, 84) and/or recombinant GST-hMet (1 mg). The immune complexes were washed extensively with buffer A and analyzed by 4–20% SDS-PAGE, followed by Western blotting with specific antisera as indicated. Blots were developed by chemiluminescence (ECL detection system, NEN).

REFERENCES

The following is a list of documents related to the above disclosure and particularly to the experimental procedures and discussions. The documents should be considered as incorporated by reference in their entirety.

1. Shatkin, A. J. (1976) Cell 9, 645–653
2. Konarska, M. M., Padgett, R. A. & Sharp, P. A. (1984) Cell 38, 731–736
3. Krainer, A. R., Maniatis, T., Ruskin, B. & Green, M. R. (1984) Cell 36, 993–1005
4. Edery, I. & Sonenberg, N. (1985) Proc. Natl. Acad. Sci. USA 82, 7590–7594
5. Hamm, J. & Mattaj, I. W. (1990) Cell 63, 109–118.
6. Shatkin, A. J. (1985) Cell 40, 223–224.
7. Furuichi, Y., LaFiandra, A. & Shatkin, A. J. (1977) Nature (London) 266, 235–239.
8. Shimotohno, K., Kodama, Y., Hashimoto, J. & Miura, K. I. (1977) Proc. Natl. Acad. Sci. USA 74, 2734–2738.
9. Shibagaki, Y., Itoh, N., Yamada, H., Nagata, S. & Mizumoto, K. (1992) J. Biol. Chem. 267, 9521–9528.
10. Mizumoto, K. & Kaziro, Y. (1987) Prog. Nucleic Acid Res. Mol. Biol. 34, 1–28.
11. Shuman, S. (1995) Prog. Nucleic Acid Res. Mol. Biol. 50, 101–129.
12. Wang, D. & Shatkin, A. J. (1984) Nucleic Acids Res. 12, 2303–2315.
13. Shuman, S., Liu, Y. & Schwer, B. (1994) Proc. Natl. Acad. Sci. USA 91, 12046–12050.
14. Yamada-Okabe, T., Shimmi, O., Doi, R., Mizumoto, K., Arisawa, M. and Yamada-Okabe, H. (1996) Microbiology 142, 2515–2523.
15. Fresco, L. D. & Buratowski, S. (1994) Proc. Natl. Acad. Sci. USA 91, 6624–6628.
16. Shuman, S. & Schwer, B. (1995) Mol. Microbiol. 17, 405–410.
17. Håkansson, K., Doherty, A. J., Shuman, S. & Wigley, D. B. (1997) Cell 89, 545–553.
18. Altschul, S. F., Gish, W., Miller, W., Myers, E. W. & Lipman, D. J. (1990) J. Mol. Biol. 215, 403–410.
19. Takagi, T., Moore, C. R., Diehn, F. & Buratowski, S. (1997) Cell 89, 867–873.
20. Schena, M., Picard, D. & Yamamoto, K. R. (1991) Methods Enzymol. 194, 389–392.
21. Yu, L. & Shuman, S. (1996) J. Virol. 70, 6162–6168.
22. Schwer, B. & Shuman, S. (1994) Proc. Natl. Acad. Sci. USA 91, 4328–4332.
23. Becker, D. M. & Guarente, L. (1991) Methods Enzymol. 194, 182–187.
24. Sikorski, R. S. & Boeke, J. D. (1991) Methods Enzymol. 194, 302–318.

25. Reinberg, D. & Roeder, R. G. (1987) J. Biol. Chem. 262, 3310–3321.
26. Lu, H., Flores, O., Weinmann, R. & Reinberg, D. (1991) Proc. Natl. Acad. Sci. USA 88, 10004–10008.
27. Kozak, M. (1987) Nucleic Acids Res. 15, 8125–8148.
28. Wang, D., Furuichi, Y. & Shatkin, A. J. (1982) Mol. Cell. Biol. 2, 993–1001.
29. Furuichi, Y., Muthukrishnan, S., Tomasz, J. & Shatkin, A. J. (1976) J. Biol. Chem. 251, 5043–5053.
30. Denu, J. M., Stuckey, J. A., Saper, M. A. & Dixon, J. E. (1996) Cell 87, 361–364.
31. Fauman, E. B. & Saper, M. A. (1996) Trends Biochem. Sci. 21, 413–417.
32. Coppola, J. A., Field, A. S. & Luse, D. S. (1983) Proc. Natl. Acad. Sci. USA 80, 1251–1255.
33. Rasumssen, E. B. & Lis, J. T. (1993) Proc. Natl. Acad. Sci. USA 90, 7923–7927.
34. Hagler, J. & Shuman, S. (1992) Science 255, 983–986.
35. Maldonado, E., Shlekhattar, R., Sheldon, M., Cho, H., Drapkin, R., Rickert, P., Lees, E., Anderson, C. W., Linn, S. & Reinberg, D. (1996) Nature (London) 381, 86–89.
36. Dahmus, M. E. (1994) Prog. Nucleic Acid Res. Mol. Biol. 48, 143–179.
37. Zawel, L. & Reinberg, D. (1993) Prog. Nucleic Acid Res. Mol. Biol. 44, 67–108.
38. Usheva, A., Maldonado, E., Goldring, A., Lu, H., Houbavi, C., Reinberg, D. & Aloni, Y. (1992) Cell 69, 871–881.
39. Maxon, M. E., Goodrich, J. A. & Tjian, R. (1994) Genes Dev. 8, 515–524.
40. Zawel, L., Kumar, K. P. & Reinberg, D. (1995) Genes Dev. 9, 1479–1490.
41. Thompson, C. M., Koleske, A. J., Chao, D. M. & Young, R. A. (1993) Cell 73, 1361–1375.
42. Kim, Y.-J., Bjorklund, S., Li, Y., Sayre, M. H. & Kornberg, R. D. (1994) Cell 77, 599–608.
43. Chao, D. M., Gadbols, E. L., Murray, P. J., Anderson, S. F., Sonu, M. S., Parvin, J. D. & Young, R. A. (1996) Nature (London) 380, 82–85.
44. Greenleaf, A. L. (1993) Trends Biochem. Sci. 18, 117–119.
45. Kuchin, S., Yeghiayan, P. & Carlson, M. (1995) Proc. Natl. Acad. Sci. USA 92, 4006–4010.
46. Mortillaro, M. J., Blencowe, B. J., Wei, X., Nakayasu, H., Du, L., Warren, S. L., Sharp, P. A. & Berezney, R. (1996) Proc. Natl. Acad. Sci. USA 93, 8253–8257.
47. O'Brien, T., Hardin, S., Greenleaf, A. & Lis, J. T. (1994) Nature (London) 370, 75–77.
48. Steinmetz, E. J. (1997) Cell 89, 491–494.
49. McCracken, S., Fong, N., Yankulov, K., Ballantyne, S., Pan, G., Greenblatt, J., Patterson, S. D., Wickens, M. & Bentley, D. L. (1997) Nature (London) 385, 357–361.
50. Georgiev, O., Moss, J. & Birnstiel, M. L. (1984) Nucleic Acids Res.12, 8539–8551.
51. Sisodia, S. S., Sollner-Webb, B. & Cleveland, D. W. (1987) Mol. Cell. Biol. 7, 3602–3612.
52. Beaton, A. R. & Krug, R. M. (1986) Proc. Natl. Acad. Sci. USA 83, 6282–6286.
53. Shuman, S., Broyles, S. S. & Moss, B. (1987) J. Biol. Chem. 262, 12372–12380.
54. Hanawalt, P. C. (1994) Science 266, 1957–1958.
55. Latchman, D. S. (1996) N. Engl. J. Med. 334, 28–33.
56. Shatkin, A. J. (1976) Cell 9, 645–653.
57. Coppola, J. A., Field, A. S. and Luse, D. S. (1983) Proc. Natl. Acad. Sci. USA 80, 1251 1255.
58. Hagler, J. and Shuman, S. (1992) Science 255, 983–986.
59. Rasumssen, E. B. and Lis, J. T. (1993) Proc. Natl. Acad. Sci. USA 90, 7923–7927.
60. Laybourn, P. J. and Dahmus, M. E. (1990) J. Biol. Chem. 265, 13165–13173.
61. Lu, H., Flores, O., Weinmann, R., and Reinberg, D. (1991) Proc. Natl. Acad. Sci. USA 88, 10004–10008.
62. Yue, Z., Maldonado, E., Pillutla, R., Cho, H., Reinberg, D., and Shatkin, A. J. (1997) Proc. Natl. Acad. Sci. USA 94, 12898–12903.
63. McCracken, S., Fong, N., Rosonina, E., Yankulov, K., Brothers, G., Siderovski, D., Hessel, A., Foster, S., Shuman, S., and Bentley, D. L. (1997) Genes and Development 11, 3306–3318.
64. Cho, E-J., Takagi, T., Moore, C. R., and Buratowski, S. (1997) Genes & Development 11, 3319–3326.
65. Yagi, Y., Mizumoto, K., and Kaziro, Y. (1983) EMBO J. 2,611–615.
66. Furuichi, Y., Muthukrishnan, S., Tomasz, J., and Shatkin, A. J. (1976) J. Biol. Chem. 251, 5043–5053
67. Moss, B. (1996) in Fields Virology, 3rd ed., eds. Fields, B. N., Knipe, D. M., and Howley, P. M. pp. 2637–2671.
68. Furuichi, Y., LaFiandra, A., and Shatkin, A. J. (1977) Nature (London) 266, 235–239.
69. Shimotohno, K., Kodama, Y., Hashimoto, J. and Miura, K. I. (1977) Proc. Natl. Acad. Sci. USA 74, 2734–2738.
70. Konarska, M. M., Padgett, R. A. and Sharp, P. A. (1984) Cell 38, 731–736.
71. Krainer, A. R., Maniatis, T., Ruskin, B., and Green, M. R. (1984) Cell 36,993–1005.
72. Edery, I., and Sonenberg, N. (1985) Proc. Natl. Acad. Sci. USA 82, 7590–7594.
73. Hamm, J., and Mattaj, I. W. (1990) Cell 63, 109–118.
74. Lewis, J. D., and Izaurralde, E. (1997) Eur. J. Biochem. 247,461–469.
75. Shatkin, A. J. (1985) Cell 40, 223–224.
76. Sonenberg, N. (1996) in Translational Control, eds. Hershey, J. W. B., Mathews, M. B., and Sonenberg, N., Cold Spring Harbor Laboratory Press, NY, pp. 245–269.
77. Morley, S. J., Curtis, P. S., and Pain, V. M. (1997) RNA 3,1085–1104.
78. LaGrandeur, T. E. and Parker, R. (1998). EMBO J. 17, 1487–1496.
79. Hsu, C. L. and Stevens, A. (1993) Mol. Cell. Biol., 13, 4826–4835.
80. Tsukamoto, T., Shibagaki, Y., Imajoh-Ohmi, S., Murakoshi, T., Suzuki, M., Nakamura, A., Gotoh, H., and Mizumoto, K. (1997) Biochem. Biophys. Res. Comm. 239, 116–122.
81. Shibagaki, Y., Itoh, N. Yamada, H., Nagata, S., and Mizumoto K. (1992) J. Biol. Chem. 267, 9521–9528.
82. Mao, X., Schwer, B., and Shuman, S. (1995) Mol. Cell. Biol. 15, 4167–4174.
83. Altschul, S. F., Gish, W., Miller, W., Myers, E. W., and Lipman, D. J. (1990) J. Mol. Biol. 215, 403–410.
84. Lu, H., Flores, O., Weinmann, R. and Reinberg, D. (1 991) Proc. Natl. Acad. Sci. USA 88, 10004–10008.
85. Ensinger, M., and Moss, B. (1976) J. Biol. Chem. 251, 5283–5291.
86. Wang, S. P., Deng, L., Ho, C. K., and Shuman, S. (1997) Proc. Natl. Acad. Sci. USA 94, 9573–9578.
87. Kagan, R. M., and Clarke, S. (1994) Arch. Biochem. Biophys. 310, 417–427.
88. Koonin, E. V. (1993) J. Gen. Virol. 74, 733–740.
89. Sripati, C. E., Groner, Y., and Warner, J. R. (1976) J. Biol. Chem., 251, 2898–2904.
90. Cory, S. and Adams, J. M. (1975) J. Mol. Biol., 99, 519–547.

91. Perry, R. P. and Kelley, D. E. (1976) Cell, 8, 433–442.
92. Friderici, K., Dovenberg, M., and Rottman, F. (1976) Biochemistry, 15, 5234–5241.
93. Schierle, B. S., Gershon, P. D., and Moss, B. (1992) Proc. Natl. Acad. Sci. USA, 89, 2897–2901.
94. Kuge, H. and Richter, J. D. (1995) EMBO J. 14, 6301–6310.
95. Mizumoto, K. and Kaziro, Y. (1987) Prog. Nucleic Acid Res. Mol. Biol., 34, 1–28.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. An isolated mammalian capping enzyme nucleic acid, or portion thereof having the following characteristics:
   (a) it encodes a polypeptide selected from the group consisting of an enzyme, or fragment thereof, said polypeptide being one with the ability to catalyze formation of an RNA 5'-terminal GpppNcap complex, wherein N is any nucleotide, nucleoside or analog thereof; and
   (b) it has the ability to hybridize under standard hybridization conditions to the sequence shown in SEQ ID NO:1 or a sequence complementary to SEQ ID NO:1.

2. An isolated nucleic acid encoding a mammalian (Guanine-7-) methyltransferase enzyme, said enzyme having the ability to catalyze formation of a methylated RNA 5'-terminal GpppN cap complex, wherein N is any nucleotide, nucleoside or analog thereof; said nucleic acid having the ability to hybridize under standard conditions to the sequence shown in SEQ ID NO:3 or a sequence complementary to SEQ ID NO:3.

3. The isolated nucleic acid of claim 1, encoding the N-terminal half of the enzyme or a portion of said N-terminal half nearest its amino terminus.

4. The isolated nucleic acid of claim 1, encoding the C-terminal half of the enzyme or a portion of said C-terminal half nearest its carboxy terminus.

5. The isolated nucleic acid of claim 1 or 2, wherein the isolated nucleic acid is selected from the group consisting of mouse, human, rabbit, rat, dog, goat and monkey nucleic acids.

6. The isolated nucleic acid of claim 1, comprising the sequence shown in SEQ ID NO:1 or a portion thereof.

7. The isolated nucleic acid of claim 1, comprising the sequence shown in SEQ ID NO:2 or a portion thereof.

8. The isolated nucleic acid of claim 2, comprising the sequence shown in SEQ ID NO:3 or a portion thereof.

9. The nucleic acid of claim 1 or 2, wherein the nucleic acid is DNA or RNA.

10. The nucleic acid of claim 1 or 2, wherein the nucleic acid is cDNA.

11. A vector comprising the nucleic acid of claim 1 or 2.

12. The vector of claim 11, wherein the vector comprises viral or plasmid DNA.

13. An expression vector comprising the nucleic acid of claim 1 or 2 and regulatory elements.

14. A host vector system which comprises the expression vector of claim 13 in a suitable host.

15. The vector of claim 11, comprising cDNA encoding mammalian capping enzyme, said vector with the structure of a plasmid deposited according to ATCC Accession No.: 203149.

16. The vector of claim 11, comprising cDNA encoding mammalian capping enzyme, said vector with the structure of a plasmid deposited according to ATCC Accession No.: 203152.

17. The vector of claim 11, comprising cDNA encoding mammalian capping enzyme, said vector with the structure of a plasmid deposited according to ATCC Accession No.: 203151.

18. The host vector system of claim 14, wherein the suitable host is selected from the group consisting of a bacterial cell, a eukaryotic cell, a mammalian cell and an insect cell.

19. A kit for catalyzing formation of a methylated RNA 5'-terminal GpppN cap complex, wherein N is any nucleotide, nucleoside or analog thereof, comprising the nucleic acid of claim 1.

20. A kit for producing protein from a DNA template through coupled transcription, catalyzed formation of RNA 5'-terminal GpppN cap complex and translation, wherein N is any nucleotide, nucleoside or analog thereof, comprising
   (a) the nucleic acid of claim 1;
   (b) a eukaryotic, cell-free cell extract, wherein the extract is from either an animal or a plant cell;
   (c) ribonucleotide triphosphates; and
   (d) RNA polymerase.

21. The kit of claim 20, wherein the nucleic acid of claim 1 further comprises an expression vector with regulatory elements.

22. A kit for producing protein from an uncapped RNA template through coupled catalyzed formation of RNA 5'-terminal GpppN cap complex and translation, wherein the kit comprises:
   (a) the nucleic acid of claim 1; and
   (b) a eukaryotic, cell-free extract, wherein the extract is from either an animal or a plant cell.

23. The kit of claim 20 further comprising a reagent from the group consisting of a nucleic acid, a protein, RNA polymerase, a ribonucleotide triphosphate mixture, a ribonuclease inhibitor, an amino acid mixture, ATP, S-adenosylmethionine, a magnesium salt, a DNA template, a capped RNA transcript, and an uncapped RNA transcript.

24. The kit of claim 20, wherein the extract is selected from the group consisting of a rabbit reticulocyte lysate and a wheat germ extract.

25. The kit of claim 22 further comprising a reagent from the group consisting of, RNA polymerase, a ribonucleotide triphosphate mixture, a ribonuclease inhibitor, an amino acid mixture, ATP, S-adenosylmethionine, a magnesium salt, a DNA template, a capped RNA transcript, and an uncapped RNA transcript.

26. The vector of claim 11, comprising cDNA encoding mammalian capping enzyme, said vector with the structure a plasmid deposited according to ATCC Accession No.:203150.

* * * * *